(12) United States Patent
Lofquist et al.

(10) Patent No.: US 10,087,440 B2
(45) Date of Patent: Oct. 2, 2018

(54) DEVICE FOR PREPARATION AND ANALYSIS OF NUCLEIC ACIDS

(71) Applicant: Micronics, Inc., Redmond, WA (US)

(72) Inventors: Alan K. Lofquist, Kirkland, WA (US); C. Frederick Battrell, Wenatchee, WA (US); Heather K. Bouzek, Seattle, WA (US)

(73) Assignee: Micronics, Inc., Redmond, WA (US)

( * ) Notice: Subject to any disclaimer, the term of this patent is extended or adjusted under 35 U.S.C. 154(b) by 31 days.

(21) Appl. No.: 14/889,374

(22) PCT Filed: May 7, 2014

(86) PCT No.: PCT/US2014/037197
§ 371 (c)(1),
(2) Date: Nov. 5, 2015

(87) PCT Pub. No.: WO2014/182847
PCT Pub. Date: Nov. 13, 2014

(65) Prior Publication Data
US 2016/0090588 A1     Mar. 31, 2016

Related U.S. Application Data

(60) Provisional application No. 61/820,582, filed on May 7, 2013, provisional application No. 61/820,573, filed
(Continued)

(51) Int. Cl.
*C12N 15/10* (2006.01)
*B01L 3/00* (2006.01)
*C12Q 1/6806* (2018.01)

(52) U.S. Cl.
CPC .... *C12N 15/1017* (2013.01); *B01L 3/502753* (2013.01); *C12Q 1/6806* (2013.01);
(Continued)

(58) Field of Classification Search
CPC .............. C12N 15/1017; C12Q 1/6806; B01L 3/502753; B01L 2400/049;
(Continued)

(56) References Cited

U.S. PATENT DOCUMENTS 3,013,467 A    12/1961   Minsky
3,799,742 A     3/1974   Coleman
(Continued)

FOREIGN PATENT DOCUMENTS

CN    1146017 A    3/1997
CN    1253625 A    5/2000
(Continued)

OTHER PUBLICATIONS

Egger et al., "Reverse Transcription Multiplex PCR for Differentiation between Polio- and Enteroviruses from Clinical and Environmental Samples," *Journal of Clinical Microbiology* 33(6):1442-1447, Jun. 1995.

(Continued)

*Primary Examiner* — Lore R Jarrett
(74) *Attorney, Agent, or Firm* — Seed Intellectual Property Law Group LLP

(57) ABSTRACT

An integrated "lab-on-a-chip" microfluidic device performs nucleic acid sample preparation and diagnostic analysis from test samples containing cells and/or particles. The device analyzes DNA or RNA targets, or both, from a common test sample. Dried and/or liquid reagents necessary for nucleic acid sample preparation and analysis are contained on the device, such that the device only requires addition of test sample. Clay mineral and alkaline buffer reagents are employed for overcoming the problems of nucleic acid degradation and contamination during sample preparation. The device may include a composite filter to separate plasma or serum from other blood constituents (Continued)

when the test sample is a blood product. The microfluidic device utilizes a plurality of microfluidic channels, inlets, valves, membranes, pumps, and other elements arranged in various configurations to manipulate the flow of the liquid sample, in particular, in order to prepare nucleic acids and perform further diagnostic analysis.

23 Claims, 6 Drawing Sheets

Related U.S. Application Data on May 7, 2013, provisional application No. 61/820,587, filed on May 7, 2013.

(52) U.S. Cl.
CPC . *B01L 2300/0681* (2013.01); *B01L 2300/087* (2013.01); *B01L 2300/0816* (2013.01); *B01L 2300/0864* (2013.01); *B01L 2400/0406* (2013.01); *B01L 2400/049* (2013.01); *B01L 2400/0481* (2013.01)

(58) Field of Classification Search
CPC ..... B01L 2400/0481; B01L 2400/0406; B01L 2300/0864; B01L 2300/0816; B01L 2300/0681; B01L 2300/087
See application file for complete search history.

(56) References Cited

U.S. PATENT DOCUMENTS

| | | |
|---|---|---|
| 3,996,345 A | 12/1976 | Ullman et al. |
| 4,104,029 A | 8/1978 | Maier, Jr. |
| 4,235,960 A | 11/1980 | Sasse et al. |
| 4,304,257 A | 12/1981 | Webster |
| 4,366,241 A | 12/1982 | Tom et al. |
| 4,373,932 A | 2/1983 | Gribnau et al. |
| 4,610,678 A | 9/1986 | Weisman et al. |
| 4,683,195 A | 7/1987 | Mullis et al. |
| 4,683,202 A | 7/1987 | Mullis |
| 4,788,729 A | 12/1988 | Walker |
| 4,798,703 A | 1/1989 | Minekane |
| 4,800,159 A | 1/1989 | Mullis et al. |
| 4,810,630 A | 3/1989 | Craig et al. |
| 4,833,332 A | 5/1989 | Robertson, Jr. et al. |
| 4,837,168 A | 6/1989 | de Jaeger et al. |
| 4,848,722 A | 7/1989 | Webster |
| 4,855,240 A | 8/1989 | Rosenstein et al. |
| 4,869,282 A | 9/1989 | Sittler et al. |
| 4,883,750 A | 11/1989 | Whiteley et al. |
| 4,889,818 A | 12/1989 | Gelfand et al. |
| 4,943,522 A | 7/1990 | Eisinger et al. |
| 4,956,302 A | 9/1990 | Gordon et al. |
| 4,965,188 A | 10/1990 | Mullis et al. |
| 5,038,852 A | 8/1991 | Johnson et al. |
| 5,075,078 A | 12/1991 | Osikowicz et al. |
| 5,075,212 A | 12/1991 | Rotbart |
| 5,100,626 A | 3/1992 | Levin |
| 5,120,643 A | 6/1992 | Ching et al. |
| 5,130,238 A | 7/1992 | Malek et al. |
| 5,141,850 A | 8/1992 | Cole et al. |
| 5,145,578 A | 9/1992 | Tokubo et al. |
| 5,160,701 A | 11/1992 | Brown, III et al. |
| 5,192,980 A | 3/1993 | Dixon et al. |
| 5,225,163 A | 7/1993 | Andrews |
| 5,234,809 A | 8/1993 | Boom et al. |
| 5,252,459 A | 10/1993 | Tarcha et al. |
| 5,270,183 A | 12/1993 | Corbett et al. |
| 5,275,785 A | 1/1994 | May et al. |
| 5,296,703 A | 3/1994 | Tsien |
| 5,304,487 A | 4/1994 | Wilding et al. |
| 5,354,668 A | 10/1994 | Auerbach |
| 5,415,994 A | 5/1995 | Imrich et al. |
| 5,420,016 A | 5/1995 | Boguslaski et al. |
| 5,427,930 A | 6/1995 | Birkenmeyer et al. |
| 5,443,890 A | 8/1995 | Öhman |
| 5,447,440 A * | 9/1995 | Davis ............... G01N 11/04 422/73 |
| 5,455,166 A | 10/1995 | Walker |
| 5,486,335 A | 1/1996 | Wilding et al. |
| 5,498,392 A | 3/1996 | Wilding et al. |
| 5,504,013 A | 4/1996 | Senior |
| 5,543,026 A | 8/1996 | Hoff et al. |
| 5,578,818 A | 11/1996 | Kain et al. |
| 5,582,989 A | 12/1996 | Caskey et al. |
| 5,587,128 A | 12/1996 | Wilding et al. |
| 5,591,645 A | 1/1997 | Rosenstein |
| 5,593,824 A | 1/1997 | Treml et al. |
| 5,602,040 A | 2/1997 | May et al. |
| 5,622,871 A | 4/1997 | May et al. |
| 5,631,734 A | 5/1997 | Stern et al. |
| 5,635,358 A | 6/1997 | Wilding et al. |
| 5,635,602 A | 6/1997 | Cantor et al. |
| 5,639,428 A | 6/1997 | Cottingham |
| 5,656,503 A | 8/1997 | May et al. |
| 5,658,723 A | 8/1997 | Oberhardt |
| 5,660,370 A | 8/1997 | Webster |
| 5,660,990 A | 8/1997 | Rao et al. |
| 5,670,381 A | 9/1997 | Jou et al. |
| 5,707,516 A | 1/1998 | Tomizawa et al. |
| 5,707,807 A | 1/1998 | Kato |
| 5,716,842 A | 2/1998 | Baier et al. |
| 5,716,852 A | 2/1998 | Yager et al. |
| 5,718,567 A | 2/1998 | Rapp et al. |
| 5,724,404 A | 3/1998 | Garcia et al. |
| 5,726,026 A | 3/1998 | Wilding et al. |
| 5,726,404 A | 3/1998 | Brody |
| 5,726,751 A | 3/1998 | Altendorf et al. |
| 5,730,850 A | 3/1998 | Kambara et al. |
| 5,747,349 A | 5/1998 | van den Engh et al. |
| 5,748,827 A | 5/1998 | Holl et al. |
| 5,759,014 A | 6/1998 | Van Lintel |
| 5,770,460 A | 6/1998 | Pawlak et al. |
| 5,798,273 A | 8/1998 | Shuler et al. |
| 5,856,174 A | 1/1999 | Lipshutz et al. |
| 5,863,502 A | 1/1999 | Southgate et al. |
| 5,863,801 A | 1/1999 | Southgate et al. |
| 5,872,710 A | 2/1999 | Kameyama |
| 5,906,602 A | 5/1999 | Weber et al. |
| 5,922,210 A | 7/1999 | Brody et al. |
| 5,922,591 A | 7/1999 | Anderson et al. |
| 5,932,100 A | 8/1999 | Yager et al. |
| 5,932,799 A | 8/1999 | Moles |
| 5,948,684 A | 9/1999 | Weigl et al. |
| 5,955,029 A | 9/1999 | Wilding et al. |
| 5,965,410 A | 10/1999 | Chow et al. |
| 5,971,158 A | 10/1999 | Yager et al. |
| 5,971,355 A | 10/1999 | Biegelsen et al. |
| 5,972,710 A | 10/1999 | Weigl et al. |
| 5,972,721 A | 10/1999 | Bruno et al. |
| 5,974,867 A | 11/1999 | Forster et al. |
| 5,989,813 A | 11/1999 | Gerdes |
| 6,001,307 A | 12/1999 | Naka et al. |
| 6,007,309 A | 12/1999 | Hartley |
| 6,007,775 A | 12/1999 | Yager |
| 6,018,616 A | 1/2000 | Schaper |
| 6,020,187 A | 2/2000 | Tam |
| 6,037,168 A | 3/2000 | Brown |
| 6,057,167 A | 5/2000 | Shieh et al. |
| 6,068,752 A | 5/2000 | Dubrow et al. |
| 6,086,740 A | 7/2000 | Kennedy |
| 6,158,712 A | 12/2000 | Craig |
| 6,168,948 B1 | 1/2001 | Anderson et al. |
| 6,171,865 B1 | 1/2001 | Weigl et al. |
| 6,184,029 B1 | 2/2001 | Wilding et al. |
| 6,210,514 B1 | 4/2001 | Cheung et al. |
| 6,210,882 B1 | 4/2001 | Landers et al. |
| 6,272,939 B1 | 8/2001 | Frye et al. |
| 6,287,850 B1 | 9/2001 | Besemer et al. |
| 6,303,389 B1 | 10/2001 | Levin et al. |
| 6,309,875 B1 | 10/2001 | Gordon |

(56) References Cited

U.S. PATENT DOCUMENTS

| | | | |
|---|---|---|---|
| 6,325,975 B1 | 12/2001 | Naka et al. |
| 6,326,211 B1 | 12/2001 | Anderson et al. |
| 6,368,876 B1 | 4/2002 | Huang et al. |
| 6,387,290 B1 | 5/2002 | Brody et al. |
| 6,390,791 B1 | 5/2002 | Maillefer et al. |
| 6,399,398 B1 | 6/2002 | Cunningham et al. |
| 6,418,968 B1 | 7/2002 | Pezzuto et al. |
| 6,431,212 B1 | 8/2002 | Hayenga et al. |
| 6,439,036 B1 | 8/2002 | Mansky |
| 6,468,807 B1 | 10/2002 | Svensson et al. |
| 6,472,161 B1 * | 10/2002 | Baugh .................... G01N 33/86 435/13 |
| 6,488,896 B2 | 12/2002 | Weigl et al. |
| 6,506,346 B1 | 1/2003 | Monro |
| 6,541,213 B1 | 4/2003 | Weigl et al. |
| 6,541,274 B2 | 4/2003 | Nagle et al. |
| 6,562,209 B1 | 5/2003 | Sullivan et al. |
| 6,569,674 B1 | 5/2003 | McGarry et al. |
| 6,576,459 B2 | 6/2003 | Miles et al. |
| 6,581,899 B2 | 6/2003 | Williams |
| 6,614,030 B2 | 9/2003 | Maher et al. |
| 6,620,273 B2 | 9/2003 | Dai et al. |
| 6,632,655 B1 | 10/2003 | Mehta et al. |
| 6,635,487 B1 | 10/2003 | Lee et al. |
| 6,637,463 B1 | 10/2003 | Lei et al. |
| 6,664,104 B2 | 12/2003 | Pourahmadi et al. |
| 6,720,411 B2 | 4/2004 | Mirkin et al. |
| 6,729,352 B2 | 5/2004 | O'Connor et al. |
| 6,731,178 B2 | 5/2004 | Gailhard et al. |
| 6,731,781 B1 | 5/2004 | Shams et al. |
| 6,743,399 B1 | 6/2004 | Weigl et al. |
| 6,748,975 B2 | 6/2004 | Hartshorne et al. |
| 6,758,107 B2 | 7/2004 | Cabuz |
| 6,767,194 B2 | 7/2004 | Jeon et al. |
| 6,787,338 B2 | 9/2004 | Wittwer et al. |
| 6,793,753 B2 | 9/2004 | Unger et al. |
| 6,815,160 B1 | 11/2004 | Chien et al. |
| 6,843,263 B2 | 1/2005 | Kuo et al. |
| 6,872,566 B2 | 3/2005 | Vischer et al. |
| 6,901,949 B2 | 6/2005 | Cox et al. |
| 6,916,113 B2 | 7/2005 | Van de Goor et al. |
| 6,951,632 B2 | 10/2005 | Unger et al. |
| 6,953,675 B2 | 10/2005 | Leung et al. |
| 6,953,676 B1 | 10/2005 | Wilding et al. |
| 6,955,738 B2 | 10/2005 | Derand et al. |
| 6,974,119 B2 | 12/2005 | Brendle et al. |
| 6,974,669 B2 | 12/2005 | Mirkin et al. |
| 7,010,391 B2 | 3/2006 | Handique et al. |
| 7,052,594 B2 | 5/2006 | Pelrine et al. |
| 7,087,414 B2 | 8/2006 | Gerdes et al. |
| 7,141,416 B2 | 11/2006 | Krutzik |
| 7,153,673 B2 | 12/2006 | Stern |
| 7,223,363 B2 | 5/2007 | McNeely et al. |
| 7,223,371 B2 | 5/2007 | Hayenga et al. |
| 7,226,562 B2 | 6/2007 | Holl et al. |
| 7,235,400 B2 | 6/2007 | Adey |
| 7,318,913 B2 | 1/2008 | Loeffler et al. |
| 7,416,892 B2 | 8/2008 | Battrell et al. |
| 7,445,926 B2 | 11/2008 | Mathies et al. |
| 7,514,212 B2 | 4/2009 | Prudent et al. |
| 7,517,651 B2 | 4/2009 | Marshall et al. |
| 7,541,147 B2 | 6/2009 | Marshall et al. |
| 7,544,506 B2 | 6/2009 | Breidford et al. |
| 7,607,641 B1 | 10/2009 | Yuan |
| 7,615,370 B2 | 11/2009 | Streit et al. |
| 7,648,835 B2 | 1/2010 | Breidford et al. |
| 7,695,683 B2 | 4/2010 | Quan et al. |
| 7,749,444 B2 | 7/2010 | Yamada et al. |
| 7,763,453 B2 | 7/2010 | Clemmens et al. |
| 7,785,776 B2 | 8/2010 | Wittwer et al. |
| 7,832,429 B2 | 11/2010 | Young et al. |
| 7,906,317 B2 | 3/2011 | Lee et al. |
| 7,955,836 B2 | 6/2011 | Clemmens et al. |
| 8,104,497 B2 | 1/2012 | Unger et al. |
| 8,104,514 B2 | 1/2012 | Fernandes et al. |
| 8,110,392 B2 | 2/2012 | Battrell et al. |
| 8,222,023 B2 | 7/2012 | Battrell et al. |
| 8,329,453 B2 | 12/2012 | Battrell et al. |
| 8,431,389 B2 | 4/2013 | Battrell et al. |
| 8,716,007 B2 | 5/2014 | Battrell et al. |
| 8,747,779 B2 | 6/2014 | Sprague et al. |
| 8,772,017 B2 | 7/2014 | Battrell et al. |
| 9,056,291 B2 | 6/2015 | Battrell et al. |
| 9,132,423 B2 | 9/2015 | Battrell et al. |
| 9,272,280 B2 * | 3/2016 | Viola .................... B01L 3/5027 |
| 2001/0046701 A1 | 11/2001 | Schulte et al. |
| 2002/0081934 A1 | 6/2002 | Murao et al. |
| 2002/0086443 A1 | 7/2002 | Bamdad |
| 2002/0137196 A1 | 9/2002 | Miles et al. |
| 2002/0160518 A1 | 10/2002 | Hayenga et al. |
| 2002/0192676 A1 | 12/2002 | Madonna et al. |
| 2002/0195152 A1 | 12/2002 | Fernandes et al. |
| 2003/0008308 A1 | 1/2003 | Enzelberger et al. |
| 2003/0013184 A1 | 1/2003 | Streit et al. |
| 2003/0032028 A1 | 2/2003 | Dace et al. |
| 2003/0073229 A1 | 4/2003 | Greenstein et al. |
| 2003/0124619 A1 | 7/2003 | Weigl et al. |
| 2003/0129756 A1 | 7/2003 | Thorne et al. |
| 2003/0136178 A1 | 7/2003 | Cabuz |
| 2003/0152927 A1 | 8/2003 | Jakobsen et al. |
| 2003/0152994 A1 | 8/2003 | Woudenberg et al. |
| 2003/0153686 A1 | 8/2003 | Onoe et al. |
| 2003/0175990 A1 | 9/2003 | Hayenga et al. |
| 2003/0215818 A1 | 11/2003 | Lorenz |
| 2003/0215825 A1 | 11/2003 | Tong |
| 2003/0224434 A1 | 12/2003 | Wittwer et al. |
| 2004/0005718 A1 | 1/2004 | Fukushima |
| 2004/0018611 A1 | 1/2004 | Ward et al. |
| 2004/0024051 A1 | 2/2004 | Holton |
| 2004/0037739 A1 | 2/2004 | McNeely et al. |
| 2004/0081997 A1 | 4/2004 | Stern |
| 2004/0115094 A1 | 6/2004 | Gumbrecht et al. |
| 2004/0121364 A1 | 6/2004 | Chee et al. |
| 2004/0124384 A1 | 7/2004 | Biegelsen et al. |
| 2004/0189311 A1 | 9/2004 | Glezer et al. |
| 2004/0209354 A1 | 10/2004 | Mathies et al. |
| 2004/0224339 A1 | 11/2004 | Numajiri et al. |
| 2004/0226348 A1 | 11/2004 | Bruce, III et al. |
| 2004/0248167 A1 | 12/2004 | Quake et al. |
| 2005/0013732 A1 | 1/2005 | Battrell et al. |
| 2005/0019792 A1 | 1/2005 | McBride et al. |
| 2005/0019898 A1 | 1/2005 | Adey et al. |
| 2005/0037397 A1 | 2/2005 | Mirkin et al. |
| 2005/0106066 A1 | 5/2005 | Saltsman et al. |
| 2005/0106742 A1 | 5/2005 | Wahl et al. |
| 2005/0118570 A1 | 6/2005 | Hollis et al. |
| 2005/0129582 A1 | 6/2005 | Breidford et al. |
| 2005/0136552 A1 | 6/2005 | Buechler |
| 2005/0142582 A1 | 6/2005 | Doyle et al. |
| 2005/0157301 A1 | 7/2005 | Chediak et al. |
| 2005/0161669 A1 | 7/2005 | Jovanovich et al. |
| 2005/0164373 A1 | 7/2005 | Oldham et al. |
| 2005/0186585 A1 | 8/2005 | Juncosa et al. |
| 2005/0205816 A1 | 9/2005 | Hayenga et al. |
| 2005/0217741 A1 | 10/2005 | Bohm |
| 2005/0221281 A1 | 10/2005 | Ho |
| 2005/0284817 A1 | 12/2005 | Fernandez et al. |
| 2006/0003440 A1 | 1/2006 | Streit et al. |
| 2006/0073484 A1 | 4/2006 | Mathies et al. |
| 2006/0076068 A1 | 4/2006 | Young et al. |
| 2006/0127886 A1 | 6/2006 | Kaylor et al. |
| 2006/0166375 A1 | 7/2006 | Hawkins et al. |
| 2006/0178568 A1 | 8/2006 | Danna et al. |
| 2006/0246575 A1 | 11/2006 | Lancaster et al. |
| 2006/0254916 A1 * | 11/2006 | Hernandez ........ B01L 3/502707 204/453 |
| 2006/0263816 A1 | 11/2006 | Laikhter et al. |
| 2006/0264782 A1 | 11/2006 | Holmes et al. |
| 2006/0275852 A1 | 12/2006 | Montagu et al. |
| 2006/0275893 A1 | 12/2006 | Ishii et al. |
| 2006/0292588 A1 | 12/2006 | Chou et al. |
| 2006/0292630 A1 | 12/2006 | Fukumoto |
| 2007/0008536 A1 | 1/2007 | Mitani et al. |
| 2007/0009383 A1 | 1/2007 | Bedingham et al. |

(56) References Cited

U.S. PATENT DOCUMENTS

| | | | |
|---|---|---|---|
| 2007/0014695 A1 | 1/2007 | Yue et al. | |
| 2007/0042427 A1 | 2/2007 | Gerdes et al. | |
| 2007/0125947 A1 | 6/2007 | Sprinzak et al. | |
| 2007/0154895 A1 | 7/2007 | Spaid et al. | |
| 2007/0183935 A1 | 8/2007 | Clemmens et al. | |
| 2007/0190525 A1 | 8/2007 | Gu et al. | |
| 2007/0219366 A1 | 9/2007 | Gumbrecht et al. | |
| 2007/0234785 A1 | 10/2007 | Beerling et al. | |
| 2007/0243603 A1 | 10/2007 | Einsle et al. | |
| 2007/0280856 A1 | 12/2007 | Ulmanella et al. | |
| 2007/0292858 A1 | 12/2007 | Chen et al. | |
| 2008/0050283 A1 | 2/2008 | Chou et al. | |
| 2008/0081341 A1 | 4/2008 | Maher et al. | |
| 2008/0124749 A1* | 5/2008 | Farnam | C12Q 1/56 435/13 |
| 2008/0226500 A1 | 9/2008 | Shikida et al. | |
| 2008/0260586 A1 | 10/2008 | Boamfa | |
| 2008/0274511 A1 | 11/2008 | Tan et al. | |
| 2008/0297792 A1 | 12/2008 | Kim et al. | |
| 2009/0000678 A1* | 1/2009 | Therriault | B01F 5/0604 137/833 |
| 2009/0017483 A1 | 1/2009 | Yamaoka et al. | |
| 2009/0047713 A1 | 2/2009 | Handique | |
| 2009/0061450 A1 | 3/2009 | Hunter | |
| 2009/0111159 A1 | 4/2009 | Brolaski et al. | |
| 2009/0148847 A1 | 6/2009 | Kokoris et al. | |
| 2009/0148933 A1* | 6/2009 | Battrell | B01F 11/0071 435/287.2 |
| 2009/0181411 A1 | 7/2009 | Battrell et al. | |
| 2009/0298059 A1 | 12/2009 | Gumbrecht et al. | |
| 2009/0325203 A1 | 12/2009 | Jenny et al. | |
| 2009/0325276 A1 | 12/2009 | Battrell et al. | |
| 2010/0041049 A1 | 2/2010 | Smith et al. | |
| 2010/0112723 A1 | 5/2010 | Battrell et al. | |
| 2010/0120129 A1 | 5/2010 | Amshey et al. | |
| 2010/0291588 A1 | 11/2010 | McDevitt et al. | |
| 2010/0303687 A1 | 12/2010 | Blaga et al. | |
| 2011/0151479 A1 | 6/2011 | Stevens et al. | |
| 2011/0207621 A1 | 8/2011 | Montagu et al. | |
| 2012/0028342 A1 | 2/2012 | Ismagilov et al. | |
| 2012/0064597 A1 | 3/2012 | Clemmens et al. | |
| 2012/0071342 A1 | 3/2012 | Lochhead et al. | |
| 2012/0115214 A1 | 5/2012 | Battrell et al. | |
| 2012/0135511 A1 | 5/2012 | Battrell et al. | |
| 2012/0156750 A1 | 6/2012 | Battrell et al. | |
| 2012/0164383 A1 | 6/2012 | Sollmann | |
| 2012/0164627 A1 | 6/2012 | Battrell et al. | |
| 2012/0177543 A1 | 7/2012 | Battrell et al. | |
| 2012/0329142 A1 | 12/2012 | Battrell et al. | |
| 2013/0011912 A1 | 1/2013 | Battrell et al. | |
| 2013/0017552 A1 | 1/2013 | Rudorfer | |
| 2013/0032235 A1 | 2/2013 | Johnstone et al. | |
| 2013/0130262 A1 | 5/2013 | Battrell et al. | |
| 2014/0349381 A1 | 11/2014 | Battrell et al. | |
| 2015/0158026 A1 | 6/2015 | Battrell et al. | |
| 2015/0321193 A1 | 11/2015 | Sprague et al. | |
| 2015/0346097 A1 | 12/2015 | Battrell et al. | |
| 2015/0352549 A1 | 12/2015 | Kolb et al. | |
| 2016/0102340 A1 | 4/2016 | Bouzek | |
| 2017/0113221 A1 | 4/2017 | Hoffman et al. | |

FOREIGN PATENT DOCUMENTS

| | | |
|---|---|---|
| CN | 102602087 A | 7/2012 |
| DE | 20 2004 012 163 U1 | 11/2004 |
| EP | 0 320 308 A2 | 6/1989 |
| EP | 0 329 822 A2 | 8/1989 |
| EP | 0 399 859 A1 | 11/1990 |
| EP | 0 517 631 A1 | 12/1992 |
| EP | 1 180 135 B1 | 8/2005 |
| EP | 1 659 405 A1 | 5/2006 |
| EP | 1 707 965 A1 | 10/2006 |
| EP | 1 726 940 A1 | 11/2006 |
| EP | 1 792 654 A2 | 6/2007 |
| EP | 2 202 328 A1 | 6/2010 |
| GB | 2 202 328 A | 9/1988 |
| JP | 52-55679 A | 5/1977 |
| JP | 61-137066 A | 6/1986 |
| JP | 7-151101 A | 6/1995 |
| JP | 2520468 Y2 | 9/1996 |
| JP | 10-82773 A | 3/1998 |
| JP | 10-504916 A | 5/1998 |
| JP | 11-508347 A | 7/1999 |
| JP | 2000-314719 A | 11/2000 |
| JP | 2003-166910 A | 6/2003 |
| JP | 2003-207454 A | 7/2003 |
| JP | 2004-028589 A | 1/2004 |
| JP | 2004-333452 A | 11/2004 |
| JP | 2005-512071 A | 4/2005 |
| JP | 2005-527303 A | 9/2005 |
| JP | 2005-531006 A | 10/2005 |
| JP | 2005-345378 A | 12/2005 |
| JP | 2006-73371 A | 3/2006 |
| JP | 2006-84459 A | 3/2006 |
| JP | 2006-90774 A | 4/2006 |
| JP | 2006-512092 A | 4/2006 |
| JP | 2006-122743 A | 5/2006 |
| JP | 2006-517029 A | 7/2006 |
| JP | 2006-227301 A | 8/2006 |
| JP | 2006-246777 A | 9/2006 |
| JP | 2006-520190 A | 9/2006 |
| JP | 2007-514142 A | 5/2007 |
| JP | 2007-532918 A | 11/2007 |
| JP | 2008-503722 A | 2/2008 |
| JP | 2008-89597 A | 4/2008 |
| JP | 2008-96375 A | 4/2008 |
| JP | 2008-537063 A | 9/2008 |
| JP | 2009-14529 A | 1/2009 |
| JP | 2009-019962 A | 1/2009 |
| JP | 2009-510337 A | 3/2009 |
| JP | 2009-513966 A | 4/2009 |
| JP | 2009-529883 A | 8/2009 |
| JP | 2009-255083 A1 | 11/2009 |
| JP | 2010-78508 A | 4/2010 |
| JP | 2010-519463 A | 6/2010 |
| JP | 2010-535346 A | 11/2010 |
| JP | 2012-516455 A | 7/2012 |
| JP | 2013-518289 A | 5/2013 |
| JP | 2015-510111 A | 4/2015 |
| JP | 2016-508197 A | 3/2016 |
| WO | 86/06488 A1 | 11/1986 |
| WO | 88/08534 A1 | 11/1988 |
| WO | 88/10315 A1 | 12/1988 |
| WO | 89/06700 A1 | 7/1989 |
| WO | 89/09284 A1 | 10/1989 |
| WO | 91/12336 A1 | 8/1991 |
| WO | 96/33399 A1 | 10/1996 |
| WO | 97/01055 A1 | 1/1997 |
| WO | 98/49543 A1 | 11/1998 |
| WO | 00/63670 A | 10/2000 |
| WO | 01/070381 A1 | 9/2001 |
| WO | 02/001184 A1 | 1/2002 |
| WO | 02/012896 A1 | 2/2002 |
| WO | 02/041994 A2 | 5/2002 |
| WO | 02/072262 A1 | 9/2002 |
| WO | 02/081934 A2 | 10/2002 |
| WO | 03/015923 A1 | 2/2003 |
| WO | 03/031977 A2 | 4/2003 |
| WO | 03/049860 A1 | 6/2003 |
| WO | 03/054523 A2 | 7/2003 |
| WO | 03/097831 A1 | 11/2003 |
| WO | 03/099355 A2 | 12/2003 |
| WO | 03/101887 A2 | 12/2003 |
| WO | 03/102546 A2 | 12/2003 |
| WO | 2004/055198 A2 | 7/2004 |
| WO | 2004/061085 A2 | 7/2004 |
| WO | 2004/065010 A2 | 8/2004 |
| WO | 2004/065930 A2 | 8/2004 |
| WO | 2005/016529 A1 | 2/2005 |
| WO | 2005/022154 A1 | 3/2005 |
| WO | 2005/066638 A1 | 7/2005 |
| WO | 2005/069015 A1 | 7/2005 |
| WO | 2005/088280 A1 | 9/2005 |

(56) References Cited

FOREIGN PATENT DOCUMENTS

| | | |
|---|---|---|
| WO | 2005/106024 A2 | 11/2005 |
| WO | 2005/118849 A1 | 12/2005 |
| WO | 2006/018811 A1 | 2/2006 |
| WO | 2006/035830 A1 | 4/2006 |
| WO | 2006/052652 A2 | 5/2006 |
| WO | 2006/076567 A2 | 7/2006 |
| WO | 2006/083833 A2 | 8/2006 |
| WO | 2006/125767 A1 | 11/2006 |
| WO | 2007/049009 A1 | 5/2007 |
| WO | 2007/064635 A1 | 6/2007 |
| WO | 2007/106579 A2 | 9/2007 |
| WO | 2007/106580 A2 | 9/2007 |
| WO | 2007/109584 A1 | 9/2007 |
| WO | 2007/137291 A1 | 11/2007 |
| WO | 2008/002462 A2 | 1/2008 |
| WO | 2008/101732 A1 | 1/2008 |
| WO | 2008/036544 A1 | 3/2008 |
| WO | 2008/070198 A2 | 6/2008 |
| WO | 2008/147382 A1 | 12/2008 |
| WO | 2009/018473 A1 | 2/2009 |
| WO | 2009/037361 A1 | 3/2009 |
| WO | 2009/105711 A1 | 8/2009 |
| WO | 2010/025302 A2 | 3/2010 |
| WO | 2010/088514 A1 | 8/2010 |
| WO | 2011/094577 A2 | 8/2011 |
| WO | 2012/071069 A1 | 5/2012 |
| WO | 2013/010674 A1 | 1/2013 |
| WO | 2013/052318 A1 | 4/2013 |
| WO | 2014/100732 A1 | 6/2014 |
| WO | 2014/182831 A1 | 11/2014 |
| WO | 2014/182847 A1 | 11/2014 |

OTHER PUBLICATIONS

Franchi et al., "Cations as Mediators of the Adsorption of Nucleic Acids on Clay Surfaces in Prebiotic Environments," *Origins of Life and Evolution of the Biosphere* 33:1-16, Feb. 2003.

Genovese et al., "Virus Variability and Its Impact on HIV and Hepatitis Therapy," *Advances in Virology* 2012:1-3, Dec. 2012.

Khanna et al., "Transformation of *Bacillus subtilis* by DNA Bound on Montmorillonite and Effect of DNase on the Transforming Ability of Bound DNA," *Applied and Environmental Microbiology* 58(6):1930-1939, Jun. 1992.

Al Zahrani et al., "Accuracy and Utility of Commercially Available Amplification and Serologic Tests for the Diagnosis of Minimal Pulmonary Tuberculosis," *Am J Respir Crit Care Med* 162:1323-1329, 2000.

Aoki et al., "Serine Repeat Antigen (SERA5) is Predominantly Expressed among the SERA Multigene Family of Plasmodium falciparum, and the Acquired Antibody Titers Correlate with Serum Inhibition of the Parasite Growth," *The Journal of Biological Chemistry* 277(49):4753347540, Dec. 2002.

Arar et al., "Synthesis and Antiviral Activity of Peptide-Oligonucleotide Conjugates Prepared by Using $N_\alpha$-(Bromoacetyl)peptides," *Bioconjugate Chem.* 6(5):573-577, 1995.

Arikan et al., "Anti-Kp 90 IgA Antibodies in the Diagnosis of Active Tuberculosis," *Chest* 114(5):1253-1257, Nov. 1998.

Birkelund, "The molecular biology and diagnostics of Chlamydia trachomatis," *Danish Medical Bulletin* 39(4):304-320, Aug. 1992.

Bongartz et al., "Improved biological activity of antisense oligonucleotides conjugated to a fusogenic peptide," *Nucleic Acids Research* 22(22):4681-4688, 1994.

Bowden et al., "Using Self-Administered Tampons to Diagnose STDs," *Aids Patient Care and STDs* 12(1):29-32, 1998.

C. Fredrick Battrell et al., "Sample-to-Answer Microfluidic Cartridge," U.S. Appl. No. 14/819,182, filed Aug. 5, 2015, 78 pages.

Cady, "Quantum dot Molecular Beacons for DNA Detection," in *Micro and Nano Technologies in Bioanalysis*, Lee et al., (eds.), Humana Press, 2009, pp. 367-379.

Carmona et al., "The use of fluorescence resonance energy transfer (FRET) peptides for measurement of clinically important proteolytic enzymes," *An Acad Bras Cienc* 81(3):381-392.

Chan et al., "Polymer surface modification by plasmas and photons," *Surface Science Reports* 24:1-54, 1996.

Chernesky et al., "Clinical Evaluation of the Sensitivity and Specificity of a Commercially Available Enzyme Immunoassay for Detection of Rubella Virus-Specific Immunoglobulin M," *J. Clin. Microbiol.* 20(3):400-404, Sep. 1984.

Chernesky et al., "Detection of Chlamydia trachomatis Antigens by Enzyme Immunoassay and Immunofluorescence in Genital Specimens from Symptomatic and Asymptomatic Men and Women," *The Journal of Infectious Diseases* 154(1):141-148, Jul. 1986.

Chou et al., "Prevention of pre-PCR mis-priming and primer dimerization improves low-copy-number amplifications," *Nucleic Acids Research* 20(7):1717-1723, 1992.

Cissell et al., "Resonance energy transfer methods of RNA detection," *Analytical and Bioanalytical Chemistry* 393(1):125-135, 2009.

Crotchfelt et al., "Detection of Neisseria gonorrhoeae and Chlamydia trachomatis in Genitourinary Specimens from Men and Women by a Coamplification PCR Assay," *J. Clin. Microbiol.* 35(6):1536-1540, Jun. 1997.

Cuzzubbo et al., "Use of Recombinant Envelope Proteins for Serological Diagnosis of Dengue Virus Infection in an Immunochromatographic Assay," *Clin. Diagn. Lab. Immunol.* 8(6):1150-1155, 2001.

D'Aquila et al., "Maximizing sensitivity and specificity of PCR by pre-amplification heating," *Nucleic Acids Research* 19(13):3749, 1991.

Dean et al., "Comprehensive human genome amplification using multiple displacement amplification," *PNAS* 99(8):5261-5266, Apr. 2002.

Detter et al., "Isothermal Strand-Displacement Amplification Applications for High-Throughput Genomics," *Genomics* 80(6):691-698, Dec. 2002.

Edelstein et al., "The BARC biosensor applied to the detection of biological warfare agents," *Biosensors & Bioelectronics* 14:805-813, 2000.

Eritja et al., "Synthesis of Defined Peptide-Oligonucleotide Hybrids Containing a Nuclear Transport Signal Sequence," *Tetrahedron* 47(24):4113-4120, 1991.

Fontana et al., "Performance of Strand Displacement Amplification Assay in the Detection of Chlamydia trachomatis and Neisseria gonorrhoeae," *Jpn. J. Infect. Dis.* 58:283-288, 2005.

Frame et al., "Identification and Typing of Herpes Simplex Virus by Enzyme Immunoassay with Monoclonal Antibodies," *J. Clin. Microbiol.* 20(2):162-166, Aug. 1984.

Freund et al., (eds.), "Film buckling, bulging, and peeling," in *Thin Film Materials: Stress, Defect Formation and Surface Evolution*, Cambridge, UK, the University of Cambridge, 2003, pp. 312-386.

Frohman, "Race: Rapid Amplification of cDNA Ends," in *PCR Protocols: A Guide to Methods and Applications*, Innis et al., (eds.), New York , Academic Press, Inc., 1990, pp. 28-38.

Gallo et al., "Study of viral integration of HPV-16 in young patients with LSIL," *J Clin Pathol* 56:532-536, 2003.

Garbassi et al., *Polymer Surfaces-From Physics to Technology*, John Wiley and Sons, Baltimore, Md., 1998, pp. 238-241.

Ghai et al., "Identification, expression, and functional characterization of MAEBL, a sporozoite and asexual blood stage chimeric erythrocyte-binding protein of Plasmodium falciparum," *Molecular & Biochemical Parasitology* 123:35-45, 2002.

Gijs, "Magnetic bead handling on-chip: new opportunities for analytical applications," *Microfluid Nanofluid* 1:22-40, 2004.

Gomes et al., "Immunoreactivity and differential developmental expression of known and putative Chlamydia trachomatis membrane proteins for biologically variant serovars representing distinct disease groups," *Microbes and Infection* 7:410-420, 2005.

Graham et al., "Magnetoresistive-based biosensors and biochips," *Trends in Biotechnology* 22(9):455-462, Sep. 2004.

Graves et al., "Development of Antibody to Measles Virus Polypeptides During Complicated and Uncomplicated Measles Virus Infections," *Journal of Virology* 49(2):409-412, Feb. 1984.

Grover et al., "Monolithic membrane valves and diaphragm pumps for practical large-scale integration into glass microfluidic devices," *Sensors and Actuators B* 89:315-323, 2003.

(56) References Cited

OTHER PUBLICATIONS

Hardt et al., "Passive micromixers for applications in the microreactor and mTAS fields," *Microfluid Nanofluid* 1:108-118, 2005.
Harris et al., "Typing of Dengue Viruses in Clinical Specimens and Mosquitoes by Single-Tube Multiplex Reverse Transcriptase PCR," *J. Clin. Microbiol.* 36(9):2634-2639, Sep. 1998.
Harrison et al., "Synthesis and hybridization analysis of a small library of peptide-oligonucleotide conjugates," *Nucleic Acids Research* 26(13):3136-3145, 1998.
Hummel et al., "Development of quantitative gene-specific real-time RT-PCR assays for the detection of measles virus in clinical specimens," *Journal of Virological Methods* 132:166-173, 2006.
Hung et al., "A specificity enhancer for polymerase chain reaction," *Nucleic Acids Research* 18(16):4953, Jun. 1990.
Innis et al., (eds.), *PCR Protocols: A Guide to Methods and Applications*, Academic Press, Inc., San Diego, California, 1990, 480 pages.
Jacobs et al., "Detection of *Streptococcus pneumoniae* Antigen in Bronchoalveolar Lavage Fluid Samples by a Rapid Immunochromatographic Membrane Assay," *J. Clin. Microbiol.* 43(8):4037-4040, 2005.
Joung et al., "Micropumps Based on Alternating High-Gradient Magnetic Fields," *IEEE Transactions on Magnetics* 36(4):2012-2014, Jul. 2000.
Kanehisa, "Use of statistical criteria for screening potential homologies in nucleic acid sequences," *Nucleic Acids Research* 12(1):203-213, Jan. 1984.
Kellogg et al., "TaqStart Antibody: "Hot Start" PCR Facilitated by a Neutralizing Monoclonal Antibody Directed Against Taq DNA Polymerase," *BioTechniques* 16(6):1134-1137, Jun. 1994.
Kennedy et al., "Protein-Protein Coupling Reactions and the Applications of Protein Conjugates," *Clinica Chimica Acta* 70(1):1-31, Jul. 1976.
Khan et al., "Antibiotic Resistance, Virulence Gene, and Molecular Profiles of Shiga Toxin-Producing *Escherichia coli* Isolates from Diverse Sources in Calcutta, India," *J. Clin. Microbiol.* 40(6):2009-2015, Jun. 2002.
Khan et al., "Prevalence and Genetic Profiling of Virulence Determinants of Non-O157 Shiga Toxin-Producing *Escherichia coli* Isolated from Cattle, Beef, and Humans, Calcutta, India," *Emerging Infectious Diseases* 8(1):54-62, Jan. 2002.
Kittigul et al., "Use of a Rapid Immunochromatographic Test for Early Diagnosis of Dengue Virus Infection," *Eur. J. Clin. Microbiol. Infect. Dis.* 21(3):224-226, Mar. 2002.
Knox et al., "Evaluation of Self-Collected Samples in Contrast to Practitioner-Collected Samples for Detection of Chlamydia trachomatis, Neisseria gonorrhoeae, and Trichomonas vaginalis by Polymerase Chain Reaction Among Women Living in Remote Areas," *Sexually Transmitted Diseases* 29(11):647-654, Nov. 2002.
Krasnoperov et al., "Luminescent Probes for Ultrasensitive Detection of Nucleic Acids," *Bioconjug. Chem.* 21(2):319-327, Feb. 2010.
Kremer et al., "Measles Virus Genotyping by Nucleotide-Specific Multiplex PCR," *J. Clin. Microbiol.* 42(7):3017-3022, Jul. 2004.
Kuipers et al., "Detection of Chlamydia trachomatis in peripheral blood leukocytes of reactive arthritis patients by polymerase chain reaction," *Arthritis & Rheumatism* 41(10):1894-1895, Oct. 1998.
Kuipers et al., "Sensitivities of PCR, MicroTrak, ChlamydiaEIA, IDEIA, and PACE 2 for Purified Chlamydia trachomatis Elementary Bodies in Urine, Peripheral Blood, Peripheral Blood Leukocytes, and Synovial Fluid," *J. Clin. Microbiol.* 33(12):3186-3190, Dec. 1995.
Kuno, "Universal diagnostic RT-PCR protocol for arboviruses," *Journal of Virological Methods* 72:27-41, 1998.
Kwoh et al., "Transcription-based amplification system and detection of amplified human immunodeficiency virus type 1 with a bead-based sandwich hybridization format," *Proc. Natl. Acad. Sci. U.S.A.* 86:1173-1177, Feb. 1989.

Lage et al., "Whole Genome Analysis of Genetic Alterations in Small DNA Samples Using Hyperbranched Strand Displacement Amplification and Array-CGH," *Genome Research* 13:294-307, 2003.
Lanciotti et al., "Rapid Detection and Typing of Dengue Viruses from Clinical Samples by Using Reverse Transcriptase-Polymerase Chain Reaction," *J. Clin. Microbiol.* 30(3):545-551, Mar. 1992.
Leclerc et al., "Meager genetic variability of the human malaria agent Plasmodium vivax," *PNAS* 101(40):14455-14460, Oct. 5, 2004.
Lee et al., "Implementation of Force Differentiation in the Immunoassay," *Analytical Biochemistry* 287:261-271, 2000.
Leung et al., "Rapid antigen detection testing in diagnosing group A b-hemolytic streptococcal pharyngitis," *Expert. Rev. Mol. Diagn.* 6(5):761-766, 2006.
Li et al., "Molecular Beacons: an optimal multifunctional biological probe," *Biochemical and Biophysical Research Communications* 373:457-461, 2008.
Lindegren et al., "Optimized Diagnosis of Acute Dengue Fever in Swedish Travelers by a Combination of Reverse Transcription-PCR and Immunoglobulin M Detection," *J. Clin. Microbiol.* 43(6):2850-2855, Jun. 2005.
Ling et al., "The Plasmodium falciparum clag9 gene encodes a rhoptry protein that is transferred to the host erythrocyte upon invasion," *Molecular Microbiology* 52(1):107-118, 2004.
Lundquist et al., "Human Recombinant Antibodies against Plasmodium falciparum Merozoite Surface Protein 3 Cloned from Peripheral Blood Leukocytes of Individuals with Immunity to Malaria Demonstrate Antiparasitic Properties," *Infect. Immun.* 74(6):3222-3231, Jun. 2006.
Luxton et al., "Use of External Magnetic Fields to Reduce Reaction Times in an Immunoassay Using Micrometer-Sized Paramagnetic Particles as Labels (Magnetoimmunoassay)," *Anal. Chem.* 76(6):1715-1719, Mar. 2004.
Mahony et al., "Chlamydia trachomatis confirmatory testing of PCR-positive genitourinary specimens using a second set of plasmid primers," *Molecular and Cellular Probes* 6:381-388, 1992.
Mahony et al., "Comparison of Plasmid- and Chromosome-Based Polymerase Chain Reaction Assays for Detecting Chlamydia trachomatis Nucleic Acids," *J. Clin. Microbiol.* 31(7):1753-1758, Jul. 1993.
Mahony et al., "Detection of Antichlamydial Immunoglobulin G and M Antibodies by Enzyme-Linked Immunosorbent Assay," *J. Clin. Microbiol.* 18(2):270-275, Aug. 1983.
Mahony et al., "Multiplex PCR for Detection of Chlamydia trachomatis and Neisseria gonorrhoeae in Genitourinary Specimens," *J. Clin. Microbiol.* 33(11):3049-3053, Nov. 1995.
Mahony, "Multiplex Polymerase Chain Reaction for the Diagnosis of Sexually Transmitted Diseases," *Clinics in Laboratory Medicine* 16(1):61-71, Mar. 1996.
Mayta et al., "Use of a reliable PCR assay for the detection of Neisseria gonorrhoeae in Peruvian patients," *Clinical Microbiology and Infection* 12(8):809-812, Aug. 2006.
Michon et al., "Naturally Acquired and Vaccine-Elicited Antibodies Block Erythrocyte Cytoadherence of the Plasmodium vivax Duffy Binding Protein," *Infect. Immun.* 68(6):3164-3171, Jun. 2000.
Migot-Nabias et al., "Immune Responses Against Plasmodium Falciparum Asexual Blood-Stage Antigens and Disease Susceptibility in Gabonese and Cameroonian Children," *Am. J. Trop. Med. Hyg.* 61(3):488-494, 1999.
Mitrani-Rosenbaum et al., "Simultaneous detection of three common sexually transmitted agents by polymerase chain reaction," *Am J Obstet Gynecol* 171(3):784-790, Sep. 1994.
Mohmmed et al., "Identification of karyopherin b as an immunogenic antigen of the malaria parasite using immune mice and human sera," *Parasite Immunology* 27:197-203, 2005.
Monis et al., "Nucleic acid amplification-based techniques for pathogen detection and identification," *Infection, Genetics and Evolution* 6:2-12, 2006.
Morré et al., "RNA Amplification by Nucleic Acid Sequence-Based Amplification with an Internal Standard Enables Reliable Detection of Chlamydia trachomatis in Cervical Scrapings and Urine Samples," *J. Clin. Microbiol.* 34(12):3108-3114, Dec. 1996.

(56) References Cited

OTHER PUBLICATIONS

Narum et al., "A novel Plasmodium falciparum erythrocyte binding protein-2 (EBP2/BAEBL) involved in erythrocyte receptor binding," *Molecular & Biochemical Parasitology* 119:159-168, 2002.
NCBI Database, GenBank Accession No. ACOL01000910, Jun. 9, 2009.
NCBI Database, GenBank Accession No. ACOL01004315, Jun. 9, 2009.
NCBI Database, GenBank Accession No. ACOL01004318, Jun. 9, 2009.
NCBI Database, GenBank Accession No. ACOL01004329, Jun. 9, 2009.
NCBI Database, GenBank Accession No. ACOL01004331, Jun. 9, 2009.
NCBI Database, GenBank Accession No. NP_473155, Jan. 3, 2007.
Nielsen et al., "Detection of Immunoglobulin G Antibodies to Cytomegalovirus Antigens by Antibody Capture Enzyme-Linked Immunosorbent Assay," *J. Clin. Microbiol.* 24(6):998-1003, Dec. 1986.
Notomi et al., "Loop-mediated isothermal amplification of DNA," *Nucleic Acids Research* 28(12):2-7, 2000.
Oeuvray et al., "Merozoite Surface Protein-3: A Malaria Protein Inducing Antibodies that Promote Plasmodium falciparum Killing by Cooperation With Blood Monocytes," *Blood* 84(5):1594-1602, Sep. 1994.
Ohara et al., "One-sided polymerase chain reaction: The amplification of cDNA," *Proc. Natl. Acad. Sci. U.S.A.* 86:5673-5677, Aug. 1989.
Ohta et al., "Enzyme-Linked Immunosorbent Assay of Influenza Specific IgA Antibody in Nasal Mucus," *Acta Paediatr Jpn.* 33(5):617-622, Oct. 1991.
Østergaard et al., "A novel approach to the automation of clinical chemistry by controlled manipulation of magnetic particles," *Journal of Magnetism and Magnetic Materials* 194:156-162, 1999.
Ozoemena et al., "Comparative Evaluation of Measles Virus Specific TaqMan PCR and Conventional PCR Using Synthetic and Natural RNA Templates," *Journal of Medical Virology* 73:79-84, 2004.
Park et al., "Polymorphisms of p53, p21 and IRF-1 and cervical cancer susceptibility in Korean Women," *Proceedings of the American Association of Cancer Research* 44, Second Edition, p. 1081, Jul. 2003.
Pfyffer et al., "Diagnostic Performance of Amplified Mycobacterium tuberculosis Direct Test with Cerebrospinal Fluid, Other Nonrespiratory, and Respiratory Specimens," *Journal of Clinical Microbiology* 34(4):834-841, Apr. 1996.
Pinder et al., "Immunoglobulin G Antibodies to Merozoite Surface Antigens Are Associated with Recovery from Choroquine-Resistant Plasmodium falciparum in Gambian Children," *Infect. Immun.* 74(5):2887-2893, May 2006.
Pingle et al., "Multiplexed Identification of Blood-Borne Bacterial Pathogens by Use of a Novel 16S rRNA Gene PCR-Ligase Detection Reaction-Capillary Electrophoresis Assay," *J. Clin. Microbiol.* 45(6):1927-1935, Jun. 2007.
Polley et al., "Vaccination for vivax malaria: targeting the invaders," *Trends in Parasitology* 20(3):99-102, Mar. 2004.
Porstmann et al., "Comparison of Chromogens for the Determination of Horseradish Peroxidase as a Marker in Enzyme Immunoassay," *J. Clin. Chem. Clin. Biochem.* 19(7):435-439, 1981.
Ranjan et al., "Mapping regions containing binding residues within functional domains of Plasmodium vivax and Plasmodium knowlesi erythrocyte-binding proteins," *PNAS* 96(24):14067-14072, Nov. 1999.
Rida et al., "Long-range transport of magnetic microbeads using simple planar coils placed in a uniform magnetostatic field," *Applied Physics Letters* 83(12):2396-2398, Sep. 2003.
Roosendaal et al., "Comparison of different primer sets for detection of Chlamydia trachomatis by the polymerase chain reaction," *J. Med. Microbiol.* 38:426-433, 1993.
Schachter et al., "Ligase Chain Reaction to Detect Chlamydia trachomatis Infection of the Cervix," *J. Clin. Microbiol.* 32(10):2540-2543, Oct. 1994.
Shi et al., "Fabrication and optimization of the multiplex PCR-based oligonucleotide microarray for detection of Neisseria gonorrhoeae, Chlamydia trachomatis and Ureaplasma urealyticum," *Journal of Microbiological Methods* 62:245-256, 2005.
Shi et al., "Natural Immune Response to the C-Terminal 19-Kilodalton Domain of Plasmodium falciparum Merozoite Surface Protein 1," *Infect. Immun.* 64(7):2716-2723, Jul. 1996.
Shu et al., "Development of Group- and Serotype-Specific One-Step SYBR Green I-Based Real-Time Reverse Transcription-PCR Assay for Dengue Virus," *J. Clin. Microbiol.* 41(6):2408-2416, Jun. 2003.
Snounou et al., "High sensitivity of detection of human malaria parasites by the use of nested polymerase chain reaction," *Molecular and Biochemical Parasitology* 61:315-320, 1993.
Soukchareun et al., "Use of Na-Fmoc-cysteine(S-thiobutyl) Derivatized Oligodeoxynucleotides for the Preparation of Oligodeoxynucleotide—Peptide Hybrid Molecules," *Bioconjugate Chem.* 9:466-475, 1998.
Staben et al., "Particle transport in Poiseuille flow in narrow channels," *International Journal of Multiphase Flow* 31:529-547, 2005.
Stetsenko et al., "Efficient Conjugation of Peptides to Oligonucleotides by 'Native Ligation'," *J. Org. Chem.* 65:4900-4908, 2000.
Sturm et al., "Vaginal tampons as specimen collection device for the molecular diagnosis of non-ulcerative sexually transmitted infections in antenatal clinic attendees," *International Journal of STD & AIDS* 15:94-98, Feb. 2004.
Tai et al., "Artificial Receptors in Serologic Tests for the Early Diagnosis of Dengue Virus Infection," *Clinical Chemistry* 52(8):1486-1491, 2006.
Tamim et al., "Cervicovaginal coinfections with human papillomavirus and chlamydia trachomatis," *Diagnostic Microbiology and Infectious Disease* 43:277-281, 2002.
TechNote 303, "Lateral Flow Tests," Bangs Laboratories, Inc., Rev. #002, Apr. 11, 2008, pp. 1-7.
Tongren et al., "Target Antigen, Age, and Duration of Antigen Exposure Independently Regulate Immunoglobulin G Subclass Switching in Malaria," *Infect. Immun.* 74(1):257-264, Jan. 2006.
Trenholme et al., "Antibody Reactivity to Linear Epitopes of Plasmodium Falciparum Cytoadherence-linked asexual gene 9 in asymptomatic children and adults from Papua New Guinea," *Am. J. Trop. Med. Hyg.* 72(6):708-713, 2005.
Tung et al., "Preparation and Applications of Peptide—Oligonucleotide Conjugates," *Bioconjugate Chem.* 11(5):605-618, Sep./Oct. 2000.
Tung et al., "Preparation of Oligonucleotide-Peptide Conjugates," *Bioconjugate Chem.* 2:464-465, 1991.
Unger et al., "Monolithic Microfabricated Valves and Pumps by Multilayer Soft Lithography," *Science* 288:113-116, Apr. 2000.
van Gemen et al., "Quantification of HIV-1 RNA in plasma using NASBAä during HIV-1 primary infection," *Journal of Virological Methods* 43: 177-188, 1993.
Van Lintel, "A Piezoelectric Micropump Based on Micromachining of Silicon," *Sensors and Actuators* 15:153-167, 1988.
Vinayagamoorthy et al., "Nucleotide Sequence-Based Multitarget Identification," *J. Clin. Microbiol.* 41(7):3284-3292, Jul. 2003.
Vivès et al., "Selective Coupling of a Highly Basic Peptide to an Oligonucleotide," *Tetrahedron Letters* 38(7):1183-1186, 1997.
Walker et al., "Strand displacement amplification—an isothermal, in vitro DNA amplification technique," *Nucleic Acids Research* 20(7):1691-1696, 1992
Walker, "Empirical Aspects of Strand Displacement Amplification," *PCR Methods and Applications* 3:1-6, 1993.
Wang et al., "Molecular engineering of DNA: molecular beacons," *Angew Chem Int Ed Engl* 48(5):856-870, 2009.
Watson et al., Molecular Biology of the Gene, 4th Ed., Benjamin Cummings Publishing Company, Menlo Park, California, Jan. 1987.
Weinstock et al., "Sexually Transmitted Diseases Among American Youth: Incidence and Prevalence Estimates, 2000," *Perspectives on Sexual and Reproductive Heath* 36(1):6-10, Jan./Feb. 2004.

(56) References Cited

OTHER PUBLICATIONS

Whiley et al., "Comparison of three in-house multiplex PCR assays for the detection of Neisseria gonorrhoeae and Chlamydia trachomatis using real-time and conventional detection methodologies," *Pathology* 37(5):364-370, Oct. 2005.

Witkin et al., "Detection of Chlamydia trachomatis by the polymerase chain reaction in the cervices of women with acute salpingitis," *Am J Obstet Gynecol* 168(5):1438-1442, May 1993.

Woehlbier et al., "Analysis of Antibodies Directed against Merozoite Surface Protein 1 of the Human Malaria Parasite Plasmodium falciparum," *Infect. Immun.* 74(2):1313-1322, Feb. 2006.

Wu et al., "The Ligation Amplification Reaction (LAR)—Amplification of Specific DNA Sequences Using Sequential Rounds of Template-Dependent Ligation," *Genomics* 4:560-569, 1989.

Yogi et al., "Clinical Evaluation of the Bladder Tumor Marker "TU-MARK-BTA"," *Hinyokika Kiyo* 37(4):335-339, Apr. 1991.

Huft et al., "Fabrication of High-Quality Microfluidic Solid-Phase Chromatography Columns," *Anal. Chem.* 85:1797-1802, 2013.

Ramachandran et al., "Dry-reagent storage for disposable lab-on-a-card diagnosis of enteric pathogens," *Proceedings of the 1st Distributed Diagnosis and Home Healthcare (D2H2) Conference*, Arlington, Virginia, USA, Apr. 2-4, 2006, pp. 16-19.

Weigl et al., "Fully integrated multiplexed lab-on-a-card assay for enteric pathogens," *Proc. of SPIE* 6112:611202-1-611202-11, 2006.

Zhang et al., "Synthesis of clay minerals," *Applied Clay Science* 50:1-11, 2010.

Cai et al., "Interactions of DNA with Clay Minerals and Soil Colloidal Particles and Protection against Degradation by DNase," *Environ. Sci. Technol.* 40:2971-2976, 2006.

\* cited by examiner

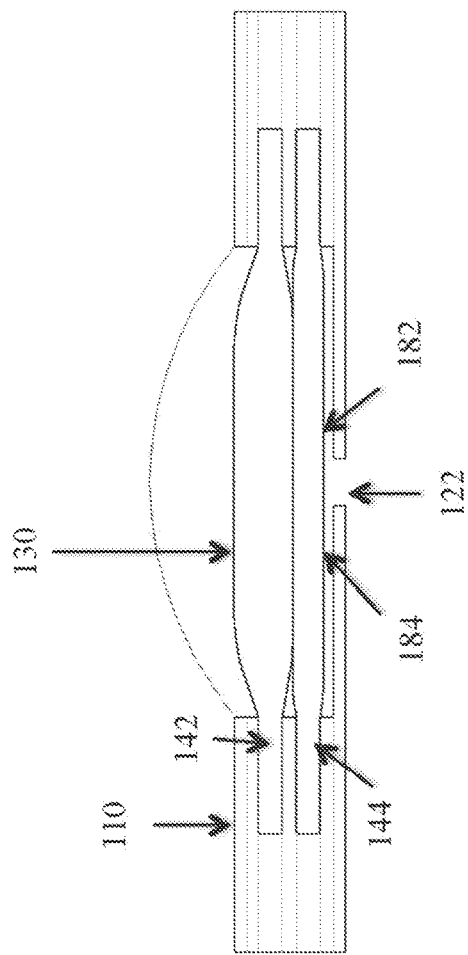
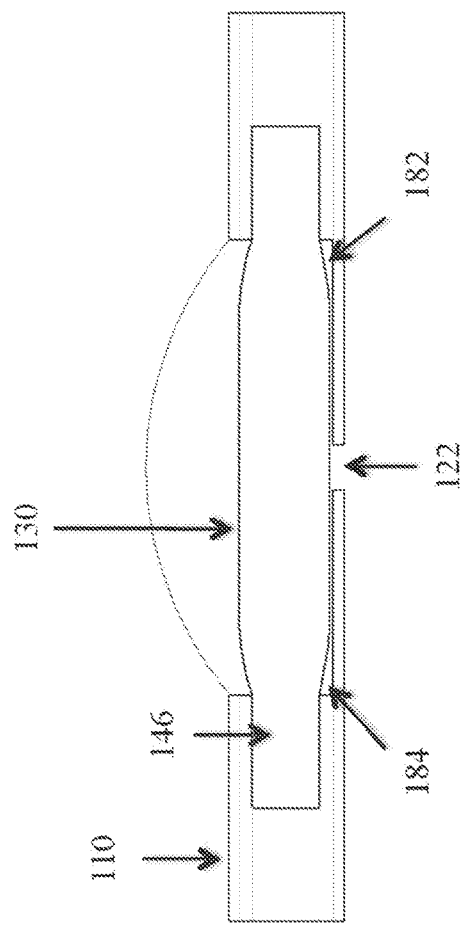
FIG. 5A
FIG. 5B

DEVICE FOR PREPARATION AND ANALYSIS OF NUCLEIC ACIDS

STATEMENT OF GOVERNMENT INTEREST

Partial funding of the work described herein was provided by a grant from the U.S. Army Medical Research Acquisition Activity under Contract No. W81XWH-10-2-0158. The U.S. Government has certain rights in this invention.

BACKGROUND

Technical Field

The present invention generally relates to microfluidic devices and methods for processing samples for molecular diagnostic applications, for example detection of target nucleic acid sequences.

Description of the Related Art

The role of molecular diagnostics is critical in today's global health care environment. In the developing world, 95% of deaths are due to a lack of proper diagnostics and the associated follow-on treatment of infectious diseases; i.e., acute respiratory infections (ARIs), malaria, HIV, and tuberculosis (TB) (Yager, P et al, Annu Rev Biomed Eng 10:107-144, 2008). Recent pandemics like the 2009 H1N1 Influenza A pandemic, have accentuated the need for tools to effectively detect and control infectious diseases. Factors like "rapid pathogen mutation rates, transformation of nonhuman pathogens into human pathogens, and recombination of non human pathogen with human pathogens" have added to the challenge of managing novel infectious diseases (Kiechle, F L et al., Clin Lab Med 29(3):555-560, 2009). Increased global mobility has aided the rapid spread of infectious diseases from region of origin to other parts of the world as seen during the 2009 H1N1 pandemic. This mobility has highlighted the need for rapid, portable diagnostic (point-of-care [POC]) devices at ports of entry to prevent global spread of infections. Current laboratory culture methods for pathogens take a day or more to provide results.

For certain other types of infections, in both the developed and developing worlds, the diagnostic tests need to be repeated periodically to measure response to therapy and monitor the disease condition. One such case is monitoring the viral load (number of viral particles per milliliter of blood) for infections like HIV (Human immunodeficiency virus) and hepatitis C. Sub-Saharan Africa is a region heavily affected by the AIDS pandemic. The lack of standard laboratory facilities and trained laboratory technicians in these regions is a serious bottleneck. Similar problems exist in medically underserved areas of the USA. Rapid, low-cost diagnostic tools that can be dispersed throughout a community for easy access, possibly even in the home, would provide substantial benefit by allowing more rapid diagnosis and monitoring of disease and infection.

Nucleic acid biomarkers are the target analytes for several infectious diseases of high global health importance, including HIV, HCV, HBV, pandemic influenza, and dengue. A major challenge in developing a simple diagnostic device to test multiple viral agents is that the genome of some viruses are comprised of DNA, while those of other viruses are comprised of RNA. A further challenge for RNA-based analytes is specimen handling that protects the integrity of these labile molecules. There are several commercially available products that address this latter problem. Most of these products are expensive, technically demanding, and/or require some form of refrigeration. These requirements cannot be easily met by miniaturized microfluidic devices with on-cartridge reagent reservoirs designed for rapid, on-site diagnostic analyses. Moreover, these requirements cannot be easily met in low-resource or remote settings, as is the case in the majority of the developing world. Thus, there is a need for a low-cost, non-instrumented, and simple-to-use diagnostic device that can be used to prepare stable samples of nucleic acids and analysis of both DNA and RNA biomarkers at the point of care (POC).

Blood is the human tissue routinely used for nucleic acid expression studies and blood-based biomarker analysis because it can be easily collected. However, whole blood often contains many factors, such as heme and heparin, which interfere with and/or inhibit, many downstream analytic procedures. Moreover, blood plasma is extremely high in ribonuclease (RNase) activity, and minimizing this activity is critical to any RNA isolation procedure. Although DNA can be prepared from clinical samples under harsh conditions and stabilized, for example, simply by spotting on filter paper and allowing to dry at room temperature, RNA preparation has typically required the use of stabilizing agents and refrigeration and/or freezing. The steps required to stabilize RNA in clinical samples are cumbersome and not amenable to microfluidic, "sample to answer" diagnostic devices.

Variations of two methods have historically been used to prepare RNA from biological samples: chemical extraction and immobilization on glass, often referred to as "solid-phase extraction." Chemical extraction methods usually use highly concentrated chaotropic salts in conjunction with acidic phenol or phenol-chloroform solutions to inactivate RNases and purify RNA from other biomolecules. These methods provide very pure preparations of RNA; however, the RNA must typically be desalted and concentrated with an alcohol precipitation step. The solid-phase extraction method, described in U.S. Pat. No. 5,234,809 to Boom et al., relies on the lysing and nuclease-inactivating properties of the chaotropic agent guanidinium thiocyanate together with the nucleic acid-binding properties of solid-state silica particles or diatoms in the presence of this agent. After silica-bound RNA is washed with a high-salt buffer containing ethanol, the RNA is eluted in a low-ionic-strength buffer.

It will be readily appreciated that sample preparation methods requiring aqueous extraction with organic solvents or chaotropic agents are tedious, hazardous, labor-intensive, and slow. Moreover, if great care is not taken in performing the procedures, residual contamination with nucleases can occur, and the sample nucleic acids will be degraded or lost. Diagnostic tests performed with such samples can give false negative results due to such degradation. False negative results can also be obtained due to chemical interference, for example from residual anionic detergents, chaotropic salts, or ethanol remaining in the sample and inhibiting target amplification procedures. If anionic detergents and proteases have been used, residual proteolytic activity can also degrade the enzymes used in target amplification and/or hybridization detection reactions and produce false negative results. Sample preparation methods based on the "Boom lysis" protocol disclosed in the '809 patent are commonly viewed as adequately addressing these problems. However, the present inventors have unexpectedly found that such extraction methods, utilizing chaotropic salts combined with solid-phase extraction, are not reliably effective in the preparation of blood or plasma samples for PCR-based detection of the HBV genome. Thus, none of the above-cited protocols is suitable for the preparation of a common sample for detection of both DNA and RNA targets from complex biological starting materials, e.g., whole blood and blood serum. This is particularly true for infectious disease diagnosis in clinical laboratory settings, where time demands are very high, and in low-resource areas where cost-effectiveness, reduction of toxic waste streams and simplicity are also of prime importance.

While progress has been made in the field, there continues to be a need in the art for point of care diagnostic devices, such as microfluidic devices, capable of isolating and analysis of nucleic acids from test samples. The present invention fulfills these needs and provides further related advantages.

BRIEF SUMMARY

Embodiments of the present invention address the above noted global health needs by providing microfluidic devices for the preparation, stabilization, and molecular analysis of nucleic acids from a test sample, such as a blood product. The present inventors have surprisingly found that a simple sample preparation protocol based on treatment with a clay mineral and alkaline buffer yields samples containing DNA and/or RNA that are suitable as immediate reagents in amplification reactions. Without being bound by theory, it is believed that the clay mineral functions to both protect nucleic acids from enzymatic degradation (due to nuclease activity) and hydrolytic degradation (due to alkaline extraction reagents). The nucleic acids samples prepared by the devices of the present invention are essentially free of nuclease activity and are superior substrates for modifying enzymes. Embodiments of the microfluidic devices of the present invention are particularly advantageous in the simultaneous detection of RNA and DNA targets from minute samples of human blood or other test samples.

In related embodiments, the present invention provides an improved integrated microfluidic device for integrating nucleic acid sample preparation with downstream molecular analysis. Notably, embodiments of the device are suitable for the preparation and analysis of both DNA and RNA from a common test sample. In certain embodiments, the devices of the invention are characterized in that the reagents for preparation of nucleic acids suitable for immediate amplification are pre-loaded into the device. These reagents include, but are not limited to, a clay mineral and an alkaline buffer.

Accordingly, embodiments of the present invention provide a microfluidic device for preparing and analyzing nucleic acids in a test sample, comprising a microfluidic channel having a first end and a second end; a sample inlet fluidly connected to the first end of the microfluidic channel for receiving a test sample; a clay treatment chamber fluidly connected to said microfluidic channel, wherein said clay treatment chamber contains a clay mineral reagent; a sample lysis chamber fluidly connected to said clay treatment chamber, wherein said sample lysis chamber contains an alkaline solution; one or more sample nucleic acid amplification and detection wells fluidly connected to said sample lysis chamber; and one or more sample outlets. In another embodiment, the present invention provides a microfluidic device for preparing and analyzing nucleic acids in a test sample wherein the clay mineral is selected from the kaolinite, smectite, or illite groups. In yet another embodiment, the clay mineral of the invention is one of talc, hallosite, bentonite, a synthetic clay mineral, or laponite. In another embodiment, the present invention provides a microfluidic device for preparing and analyzing nucleic acids in a test sample wherein the alkaline solution is KOH, NaOH, or LiOH. In another embodiment, the present invention provides a microfluidic device for preparing and analyzing nucleic acids in a test sample that further comprises a neutralization chamber downstream of the lysis chamber that contains an acid reagent. In other embodiments, the acidic solution is HCl, $C_2H_4O_2$, or $H_2SO_4$. In another embodiment, the present invention provides a microfluidic device for preparing and analyzing nucleic acids in a test sample, wherein the test sample comprises one or more infectious agents. In another embodiment, the infectious agents are viral agents. In yet another embodiment, the infectious agents are at least two viral agents. In yet another embodiment, the infectious agents are a DNA virus and a RNA virus. In yet another embodiment, the infectious agents are HBV and HCV or HIV. In another embodiment, the present invention provides a microfluidic device for preparing and analyzing nucleic acids in a test sample wherein the test sample comprises blood, plasma, serum, urine, saliva, sputum, respiratory lavage, tears, or tissue swabs. In another embodiment, the present invention provides a microfluidic device for preparing and analyzing nucleic acids in a test sample wherein the device further comprises an on-device pump fluidly connected to the second end of the microfluidic channel. In another embodiment, the present invention provides a microfluidic device for preparing and analyzing nucleic acids in a test sample wherein the device further comprises a composite membrane interposed between the sample inlet and the first end of the microfluidic channel, wherein the composite membrane is capable of removing selected particles from the blood. In other embodiments, the composite membrane may be comprised of a material that activates blood coagulation. In another embodiment, that composite membrane may be comprised of a glass filter.

Methods for using the microfluidic devices for preparation and or analysis of nucleic acid containing samples are also provided. For example, in one embodiment the methods comprise:

a) introducing a sample suspected of containing the nucleic acid of interest into any of the disclosed microfluidic devices;

b) contacting the sample with a clay mineral in the microfluidic device; and c) lysing the sample in the microfluidic device.

In some embodiments, the methods further comprise amplifying the lysed sample in the microfluidic device to obtain an amplified sample and optionally detecting the nucleic acid of interest in the amplified sample.

Use of the microfluidic devices for isolating a nucleic acid of interest is also provided. In some embodiments, the use further comprises amplifying the nucleic acid of interest and optionally detecting the nucleic acid of interest.

BRIEF DESCRIPTION OF THE DRAWINGS

FIGS. 5 A-B are cross-sectional views illustrating the operation of a first and second embodiment of a composite membrane in accordance with aspects of the present invention.

DETAILED DESCRIPTION

Figure 1:
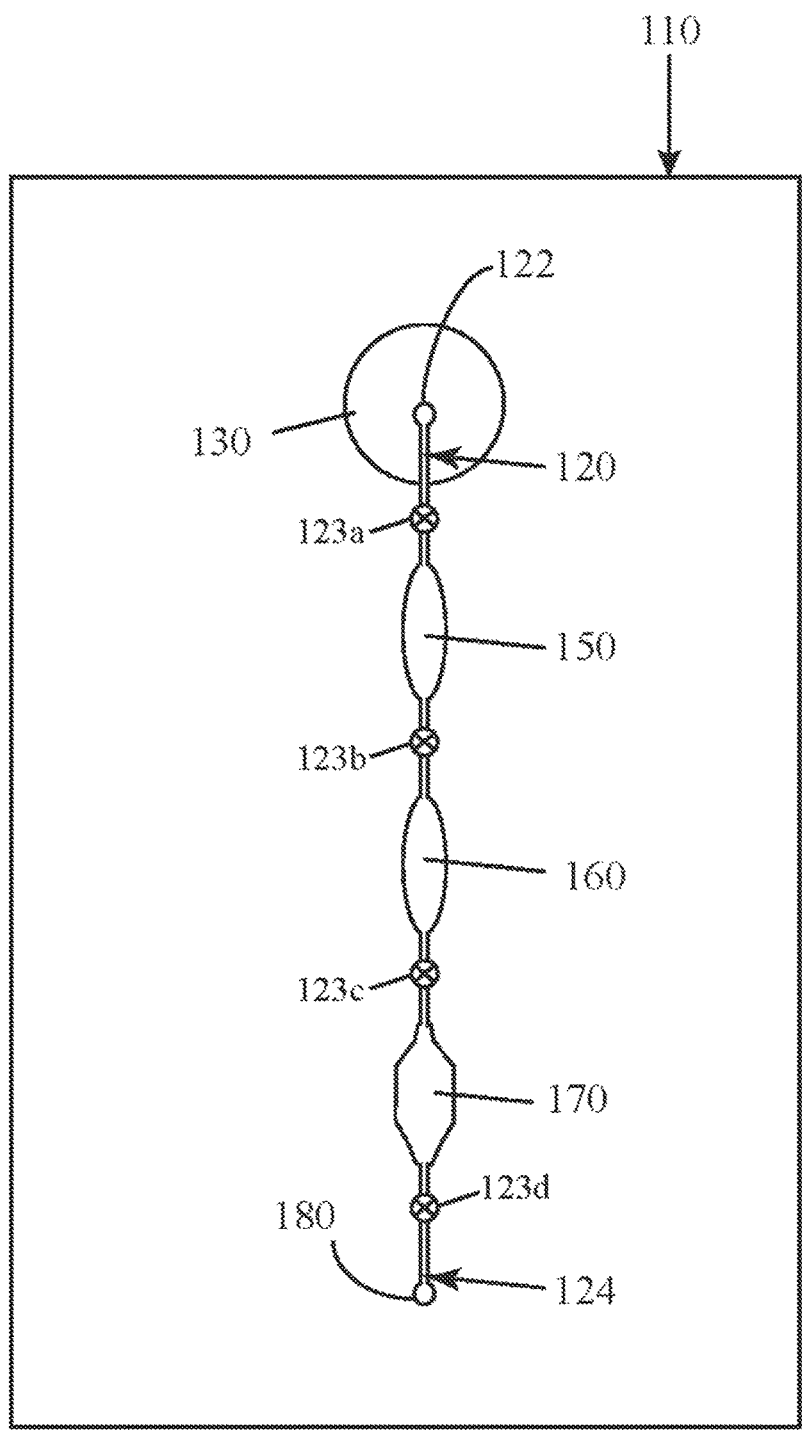
FIG. 1 is a schematic view illustrating the operation of a first embodiment of a microfluidic device in accordance with aspects of the present invention.

The present inventors have surprisingly found that the combination of a clay mineral and an alkaline buffer can be used to prepare nucleic acids from complex biological test samples for molecular analytic procedures, such as PCR. Advantageously, these reagents can be used to prepare a single test sample for the detection of both DNA and a RNA target molecules without the need for further purification or isolation of the nucleic acids, offering a vast improvement over the state-of-the-art. Without being bound by theory, it is believed that the clay mineral provides several beneficial effects, including, but not limited to: protection of nucleic acids from hydrolysis under alkaline conditions; protection of nucleic acids from nuclease-mediated degradation; protection of downstream assay reagents, such as DNA polymerases, from inhibitors and other contaminants present in the test sample; and general buffering properties.

The present invention relates to microfluidic devices comprising on-board clay mineral and alkaline buffers reagents for the preparation and analysis of nucleic acids samples. In some embodiments, the devices further comprise a plurality of microfluidic channels, inlets, valves, membranes, pumps, and other elements arranged in various configurations manipulate the flow of the fluid sample in order to extract nucleic acids from the sample and to perform optional subsequent molecular analysis. The devices of the invention may further comprise a composite membrane for the separation of a serum sample from a whole blood sample. In the following description, certain specific embodiments of the present devices and methods are set forth, however, persons skilled in the art will understand that the various embodiments and elements described below may be combined or modified without deviating from the spirit and scope of the invention.

1. Definitions

Test samples: Test samples include biological samples or "biosamples," which may be clinical specimens. Representative biosamples include, for example: blood, serum, plasma, buffy coat, saliva, wound exudates, pus, lung and other respiratory aspirates, nasal aspirates and washes, sinus drainage, bronchial lavage fluids, sputum, medial and inner ear aspirates, cyst aspirates, cerebral spinal fluid, stool, diarrhoeal fluid, urine, tears, mammary secretions, ovarian contents, ascites fluid, mucous, gastric fluid, gastrointestinal contents, urethral discharge, synovial fluid, peritoneal fluid, meconium, vaginal fluid or discharge, amniotic fluid, semen, penile discharge, or the like may be tested. Assay from swabs or lavages representative of mucosal secretions and epithelia are acceptable, for example mucosal swabs of the throat, tonsils, gingival, nasal passages, vagina, urethra, rectum, lower colon, and eyes, as are homogenates, lysates and digests of tissue specimens of all sorts. Mammalian cells are acceptable samples. Besides physiological or biological fluids, samples of water, industrial discharges, food products, milk, air filtrates, and so forth are also test specimens. In some embodiments, test samples are placed directly in the device; in other embodiments, pre-analytical processing is contemplated.

Bioassay Target Molecule: or "nucleic acid of interest," or "target molecule," includes a nucleic acid or nucleic acids. Target nucleic acids include genes, portions of genes, regulatory sequences of genes, mRNAs, rRNAs, tRNAs, siRNAs, cDNA and may be single stranded, double stranded or triple stranded. Some nucleic acid targets have polymorphisms, deletions and alternate splice sequences.

Clay mineral: or "clay" refers to any of a group of hydrous aluminum or magnesium silicates (including phyllosilicates) with a layer (sheet like) structure and very small particle size (customarily less than two micrometers). Clay minerals may contain significant amounts of iron, alkali metals, or alkaline earths. Clay minerals form the main mineral stock of naturally occurring clays and clay stones and are produced from such geologic deposits. Clay minerals may also be derived from other natural sources, such as silt stones, clay slates and some sands and sandstones. Clay minerals may also be produced synthetically.

Phyllosilicate: includes a broad class of minerals described as sheet silicates, which form parallel sheets of silicate tetrahedra with a composition of $Si_2O_5$ or a 2:5 ratio of silicon to oxygen. Phyllosilicates include the following groups: the serpentine group of antigorite and chrysotile, the apophyllite group, the prehnite group, and the clay mineral groups described below. Any of these phyllosilicates, including the mineral known as talc, is suitable for use in the present invention.

Pathogen: an organism associated with an infection or infectious disease.

Pathogenic condition: a condition of a mammalian host characterized by the absence of health, i.e., a disease, infirmity, morbidity, or a genetic trait associated with potential morbidity.

Various embodiments include microfluidic devices capable of analysis of test samples comprising one or more target infectious agents. Exemplary target infectious agents include microorganisms and/or viruses with either a DNA-based genome or an RNA-based genome. In some embodiments, suitable viruses include, but are not limited to, Hepatitis B virus (HBV), Hepatitis C virus (HCV), human immunodeficiency viruses (HIV) I and II, influenza A virus, influenza B virus, respiratory syncytial viruses (RSV) A and B, human metapneumovirus (MPV), and/or herpes simplex viruses (HSV) I and/or II.

In other embodiments, viral infectious agents present in a test sample include, but are not limited to, influenza A, influenza B, RSV (respiratory syncytial virus) A and B, human immunodeficiency virus (HIV), human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, reo viruses, Norovirus, human metapneumovirus (MPV), Herpes simplex virus 1 and 2 (HSV-1 and HSV-2), West Nile virus, Yellow fever virus, Varicella zoster virus (VZV), Rabies virus, Rhinovirus, Rift Valley fever virus, Marburg virus, mumps virus, measles virus, Epstein-Barr Virus (EBV), human papilloma virus (HPV), Ebola virus, Colorado tick fever virus (CTFV), and/or rhinoviruses.

In different embodiments, bacterial infectious agents in a test sample include, but are not limited to, *Escherichia coli, Salmonella, Shigella, Campylobacter, Klebsiella, Pseudomonas, Listeria monocytogenes, Mycobacterium tuberculosis, Mycobacterium avium*-intracellulare, *Yersinia, Francisella, Pasteurella, Brucella, Clostridia, Bordetella*

*pertussis, Bacteroides, Staphylococcus aureus, Streptococcus pneumonia*, B-Hemolytic strep., *Corynebacteria, Legionella, Mycoplasma, Ureaplasma, Chlamydia, Clostridium difficile, Gardnerella, Trichomonas vaginalis, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis*, Rickettsial pathogens, *Nocardia*, Acitnomycetes and/or *Acinetobacter.*

In still other embodiments, fungal infectious agents in a test sample include, but are not limited to, *Cryptococcus neoformans, Blastomyces dermatitidis, Histoplasma capsulatum, Coccidioides immitis, Paracoccidioides brasiliensis, Candida albicans, Aspergillus fumigautus*, Phycomycetes (*Rhizopus*), *Sporothrix schenckii*, Chromomycosis, and/or Maduromycosis.

In more embodiments, parasitic agents present in a test sample include, but are not limited to, *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidium, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis*, trematodes, *Diphyllobothrium latum, Taenia* spp., *Pneumocystis carinii*, and/or *Necator americanis.*

Nucleic acid: The terms "nucleic acid," "polynucleotide," and "oligonucleotide" are used herein to include a polymeric form of nucleotides of any length, including, but not limited to, ribonucleotides and deoxyribonucleotides. Relatively short nucleic acid polymers are often used as "primers" or "probes." The definition encompasses nucleic acids from natural sources which can be methylated or capped, and also synthetic forms, which can contain substitute or derivatized nucleobases and may be based on a peptide backbone. Nucleic acids are generally polymers of adenosine, guanine, thymine, and cytosine and their "deoxy-" forms, but may also contain other pyrimidines such as uracil and xanthine, or spacers and universal bases such as deoxyinosine. Deoxynucleic acids may be single-stranded or double-stranded depending on the presence or absence of complementary sequences, and on conditions of pH, salt concentration, temperature, and the presence or absence of certain organic solvents such as formamide, n,n-dimethylformamide, dimethylsulfoxide, and n-methylpyrrolidinone.

"Target nucleic acid sequence" or "template": As used herein, the term "target" refers to a nucleic acid sequence in a biosample that is to be amplified in the assay by a polymerase and detected. The "target" molecule can be present as a "spike" or as an uncharacterized analyte in a sample, and may consist of DNA, cDNA, gDNA, RNA, mRNA, rRNA, or miRNA, either synthetic or native to an organism. The "organism" is not limited to a mammal. The target nucleic acid sequence is a template for synthesis of a complementary sequence during amplification. Genomic target sequences are denoted by a listing of the order of the bases, listed by convention from 5' end to 3' end.

Reporter, "Label" or "Tag": refers to a biomolecule or modification of a biomolecule that can be detected by physical, chemical, electromagnetic and other related analytical techniques. Examples of detectable reporters include, but are not limited to, radioisotopes, fluorophores, chromophores, mass labels, electron dense particles, magnetic particles, dyed particles, QDots, spin labels, molecules that emit chemiluminescence, electrochemically active molecules, enzymes, cofactors, enzymes linked to nucleic acid probes, and enzyme substrates. Reporters are used in bioassays as reagents, and are often covalently attached to another molecule, adsorbed on a solid phase, or bound by specific affinity binding.

Probe: A "probe" is a nucleic acid capable of binding to a target nucleic acid by complementary base pairing with sufficient complementarity to form a stable double helix at room temperature. Probes may be labeled with reporter groups. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. Tools for selection of a probe sequence, length, and hybridization conditions are generally familiar to those skilled in the art.

Amplification: As used here, the term "amplification" refers to a "template-dependent process" that results in an increase in the concentration of a nucleic acid sequence relative to its initial concentration. A "template-dependent process" is a process that involves "template-dependent extension" of a "primer" molecule. A "primer" molecule refers to a sequence of a nucleic acid that is complementary to a known portion of the target sequence. A "template dependent extension" refers to nucleic acid synthesis of RNA or DNA wherein the sequence of the newly synthesized strand of nucleic acid is dictated by the rules of complementary base pairing of the target nucleic acid and the primers.

Amplicon refers to a double stranded DNA product of a prior art amplification means, and includes double stranded DNA products formed from DNA and RNA templates.

Two-tailed Amplicon refers to a double stranded DNA product of an amplification means in which tagged primer pairs are covalently incorporated, a first primer conjugated with a peptide hapten or epitope, a second primer conjugated with an affinity reporter, tag or "ligand." As used herein, the two-tailed amplicon functions as a "hetero-bifunctional" tether, and forms a molecular detection complex on a solid substrate.

Primer: as used herein, is a single-stranded polynucleotide or polynucleotide conjugate capable of acting as a point of initiation for template-directed DNA synthesis in the presence of a suitable polymerase and cofactors. Primers are generally at least 7 nucleotides long and, more typically range from 10 to 30 nucleotides in length, or longer. The term "primer pair" refers to a set of primers including a 5' "forward" or "upstream" primer that hybridizes with the complement of the 5' end of the DNA template to be amplified and a 3' "reverse" or "downstream" primer that hybridizes with the 3' end of the sequence to be amplified. Note that both primers have 5' and 3' ends and that primer extension always occurs in the direction of 5' to 3'. Therefore, chemical conjugation at or near the 5' end does not block primer extension by a suitable polymerase. Primers may be referred to as "first primer" and "second primer," indicating a primer pair in which the identity of the "forward" and "reverse" primers is interchangeable. Additional primers may be used in nested amplification.

Polymerases are enzymes defined by their function of incorporating nucleoside triphosphates, or deoxynucleoside triphosphates, to extend a 3' hydroxyl terminus of a primer molecule. For a general discussion concerning polymerases, see Watson, J. D. et al, (1987) Molecular Biology of the Gene, 4th Ed., W. A. Benjamin, Inc., Menlo Park, Calif. Examples of polymerases include, but are not limited to, *E. coli* DNA polymerase I, "Klenow" fragment, Taq-polymerase, T7 polymerase, T4 polymerase, T5 polymerase and reverse transcriptase. Examples of reverse transcriptases include HIV-1 reverse transcriptase from the human immunodeficiency virus type 1, telomerase, M-MuLV reverse transcriptase from the Moloney murine leukemia virus, and AMV reverse transcriptase from the avian myeloblastosis virus.

It should be noted that reverse transcriptase is commonly used in research to apply the polymerase chain reaction technique to RNA targets. The classical PCR technique can only be applied directly to DNA, but by using reverse transcriptase to synthesize cDNA from RNA, PCR analysis of RNA targets is possible. The technique is collectively called Reverse Transcription-Polymerase Chain Reaction (RT-PCR).

Complementary (with respect to nucleic acids) refers to two single-stranded nucleic acid sequences that can hybridize to form a double helix. The matching of base pairs in the double helix of two complementary strands is not necessarily absolute. Selectivity of hybridization is a function of temperature of annealing, salt concentration, and solvent, and will generally occur under low stringency when there is as little as 55% identity over a stretch of at least 14-25 nucleotides. Stringency can be increased by methods well known in the art. See M. Kanehisa, Nucleic Acids Res. 12:203 (1984). Regarding hybridization of primers, a primer that is "perfectly complementary" has a sequence fully complementary across the entire length of the primer and has no mismatches. A "mismatch" refers to a site at which the base in the primer and the base in the target nucleic acid with which it is aligned are not complementary.

Pre-loading is a term that means that reagents are added to the device prior to its end use, for example, during the device's manufacture. As such, solid reagents may be deposited on the device, for example, by drying a solution of the reagent by allowing the solvent in the reagent to evaporate. Alternatively, reagents may be pre-loaded in dehydrated form as disclosed in U.S. Patent Application Pub. No. 2012/0156750 to Batten et al., the entire contents of which is herein incorporated by reference.

Reagent refers broadly to any chemical or biochemical agent used in a reaction, including enzymes. A reagent can include a single agent which itself can be monitored (e.g., a substance that is monitored as it is heated) or a mixture of two or more agents. A reagent may be living (e.g., a cell) or non-living. Exemplary reagents for a nucleic acid amplification reaction include, but are not limited to, buffer, metal ion (for example magnesium salt), chelator, polymerase, primer, template, nucleotide triphosphate, label, dye, nuclease inhibitor, and the like. Reagents for enzyme reactions include, for example, substrates, chromogens, cofactors, coupling enzymes, buffer, metal ions, inhibitors and activators. Not all reagents are reactants.

Specificity: Refers to the ability of an assay to reliably differentiate a true positive signal of the target biomarker from any background, erroneous or interfering signals.

Sensitivity: Refers to the lower limit of detection of an assay where a negative can no longer be reliably distinguished from a positive.

Stability: during storage, any compositional change measured in a parameter, for example activity, concentration, degradation, viscosity, pH, or particle composition, that is greater than 10% over time, denotes instability. Changes less than or equal to 10% connote stability. The time period over which stability is measured is relative depending on the intended utility of the composition. Accelerated stability at higher temperature is sometimes taken as a more speedy way of extrapolating stability over longer periods of time than are actually measured.

Endpoint: "Endpoint" or "datapoint" is used here as shorthand for a "result" from either qualitative or quantitative assays, and may refer to both stable endpoints where a constant plateau or level of reactant is attained, and to rate reactions, where the rate of appearance or disappearance of a reactant or product as a function of time (i.e., the slope) is the datapoint.

Microfluidic cartridge: a "device," "card," or "chip" with fluidic structures and internal channels having microfluidic dimensions. These fluidic structures may include chambers, valves, vents, vias, pumps, inlets, nipples, and detection means, for example. Generally, microfluidic channels are fluid passages having at least one internal cross-sectional dimension that is less than about 500 μm and typically between about 0.1 μm and about 500 μm Microfluidic channels are fluid passages having at least one internal cross-sectional dimension that is less than 600 μm. The microfluidic flow regime is characterized by Poiseuille or "laminar" flow. The particle volume fraction and ratio of channel diameter to particle diameter (D/d) has a measurable effect on flow characteristics. (See for example, Staben M E et al. 2005. Particle transport in Poiseuille flow in narrow channels. Intl J Multiphase Flow 31:529-47, and references cited therein, incorporated herein by reference in its entirety).

Microfluidic cartridges may be fabricated from various materials using techniques such as laser stenciling, embossing, stamping, injection molding, masking, etching, and three-dimensional soft lithography. Laminated microfluidic cartridges are further fabricated with adhesive interlayers or by thermal adhesiveless bonding techniques, such by pressure treatment of oriented polypropylene. The microarchitecture of laminated and molded microfluidic cartridges can differ.

Microfluidic channel: also termed "microchannel," is a fluid channel having variable length, but one dimension in cross-section less than 500 μm. Microfluidic fluid flow behavior in a microfluidic channel is highly non-ideal and laminar and may be more dependent on wall wetting properties, roughness, liquid viscosity, adhesion, and cohesion than on pressure drop from end to end or cross-sectional area. The microfluidic flow regime is often associated with the presence of "virtual liquid walls" in the channel. However, in larger channels, head pressures of 10 psi or more can generate transitional flow regimes bordering on turbulent, as can be important in rinse steps of assays.

Microchannels constructed of layers formed by extrusion molding may have more rounded channel profiles and a radius on each "via." The internal channel surfaces of injection molded parts are also somewhat smoother. The flow characteristics of the channels are significant because of the profound surface effects in the microflow regime. Surface tension and viscosity compound surface roughness effects. The most narrow dimension of a channel has the most profound effect on flow. It follows that flow in channels that are based on rectangular or circular cross-sectional profiles is controlled by the diagonal width or diameter, and design is typically varied to take advantage of this behavior. Reduction of taper in the direction of flow leads to a wicking effect for diameters below 200 microns. Conversely, flow can be stopped by opening up a channel to form a bulb unless pressure is applied. Vias in a channel can be designed to promote directional flow, a sort of solid state check valve.

As used herein, the term "downstream" means that, in use, a sample passes sequentially through the different parts of the device. While the term "downstream" includes within its scope two parts of the device being in direct fluid communication, it also includes within its scope when the two parts are separated by, for example, a valve or another part of the device. The term "integrated" means that two different parts of the device are combined into a single unit, so that, for example, the same part of the device can serve to filter the sample and act as a lysis unit. When the term "integrated" is applied to the device of the first and second aspects of the present invention combined with a nucleic acid amplification unit, it means that the two parts of the system are connected to one another so that, in use, they are in fluid communication with one another. In another aspect, the term "integrated" means that the different parts of the device are preferably formed on a common substrate. The term "connected" when applied to two parts of the device means that the two parts may be in direct fluid communication with one another (e.g., through either being joined directly together or joined through a channel) or may be separated from one another by, for example, a valve or another part of a device. Preferably, the term "connected to" means that two parts of the device are directly joined to one another.

Microfluidic pumps: include for example, bulbs, bellows, diaphragms, or bubbles intended to force movement of fluids, where the substructures of the pump have a thicknesses or other dimension of less than 1 millimeter. Such pumps include the mechanically actuated recirculating pumps described in U.S. Pat. No. 6,743,399 to Weigl and U.S. 2005/0106066 to Saltsman, commonly assigned to the applicant and incorporated herein by reference in their entireties. Such pumps may be robotically operated or operated by hand. Electroosmotic pumps are also provided. Such pumps can be used in place of external drives to propulse the flow of solubilized reagents and sample in microfluidic device-based assays.

Bellows ("Finger") Pump: is a device formed as a cavity, often cylindrical in shape, bisected in coronal section by an elastomeric diaphragm to form a first and a second half-chamber which are not fluidically connected. The diaphragm is controlled by a pneumatic pulse generator connected to the first half-chamber. Positive pressure above the diaphragm distends it, displacing the contents of the second half-chamber, negative gauge pressure (suction) retracts it, expanding the second half chamber and drawing fluid in. By half-chamber, it should be understood that the effective area of the diaphragm is the lesser of the volume displacement under positive pressure and the volume displacement under suction pressure, and it thus optimal when the first and second half chambers are roughly symmetrical or equal in volume above and below the diaphragm. The second half-chamber is connected to a fluid in-port and out-port. The fluid in-port and out-port may be separate ports or a single port, but in either case, are under valve control. As described above, a pneumatic pulse generator is pneumatically connected to the first half-chamber, generally by a microchannel, which is also valved. In the complete apparatus, pneumatic actuation is programmable. Thus, programmable pneumatic pressure logic used by the pulse generator has two functions, to actuate the diaphragm on signal, and to open and close valves on signal. When the pulse generator is off-cartridge, nipples or inlets, a pneumatic manifold and solenoid valves are provided.

In use, fluid enters the second half-chamber of a bellows pump through the inlet valve when negative pressure is applied to the diaphragm (or passively, when fluid is pushed in by a second bellows pump). Then, when positive pressure is applied to the diaphragm, the fluid contents of the chamber are displaced out through the outlet valve. Similarly, positive and negative pressure signals control valve opening and closing. By supplying a train of positive and negative pressure pulses to a diaphragm, fluid can be moved in and out of a bellows pump chamber. This fluid motion becomes directional by the application of synchronized valve logic, thus the pumping action.

Microfluidic valves: include a genus of hydraulic, mechanic, pneumatic, magnetic, and electrostatic actuator flow controllers with at least one dimension smaller than 500 um. A representative flap valve of the genus is described in U.S. Pat. No. 6,431,212, which is incorporated by reference in its entirety. Also included are check valves. One class of valves refers to a configuration in which a flow channel and a control channel intersect and are separated by an elastomeric membrane that can be deflected into or retracted from the flow channel in response to an actuation force in the control channel. Patents describing species of microfluidic valves include U.S. Pat. Nos. 5,971,355, 6,418,968, 6,518,99, 6,620,273, 6,748,975, 6,767,194, 6,901,949, and U.S. Patent Application 2002/0195152 and 2005/02005816, several of which are commonly assigned to the applicant, and all of which are incorporated herein by reference.

Check valve: is a one way valve. Microscale versions of ball-spring, flap, and flip-flop valves are check valves.

Passive shut-off valves: are wettable inserts or coatings in microfluidic channels that swell when immersed, closing the microchannel off to further flow in either direction. Analogously, "surface tension valves" consisting of a ring of hydrophobic material on the walls of a microchannel have been disclosed to delay or stop the flow of a reagent. Stop flow can also be achieved by widening the taper of a microfluidic channel diameter.

Self-priming: connotes a microfluidic channel that is fabricated from a material or is treated so that the channel is wettable and capillary flow begins generally without the need to prime the channel.

Via: A step in a microfluidic channel that provides a fluid pathway from one substrate layer to another substrate layer above or below, characteristic of laminated devices built from layers.

Pillow: an on-board reagent pack formed from a deformable sacculus, for example a mylar microbag, optionally enclosed in a pneumatically actuated device for puncturing to bag to release its contents at a controlled time. Co-laminates of a metal and a plastic are preferred for stability considerations.

Blister pack: an on-board reagent pack under a deformable (or elastic) diaphragm. Used to deliver reagents by pressurizing the diaphragm and may appose a "sharp," such as a metal chevron, so that pressure on the diaphragm ruptures the "pillow" (see pillow). These may be used with check valves or closable vents to produce directional fluid flow and reagent delivery. Elastic diaphragms are readily obtained from polyurethane, polysilicone and polybutadiene, and nitrile for example (see elastomer). Deformable, inelastic diaphragms are made with polyethylene terephthalate (PET), mylar, polypropylene, polycarbonate, or nylon, for example. Other suitable materials for the deformable film include parafilm, latex, foil, and polyethylene terephthalate. Key factors in selecting a deformable film include the yield point and the deformation relaxation coefficient (elastic modulus).

Isolation or "isolated": "Forward isolation" refers here to protection of the user from exposure to clinical materials potentially contaminated with an infectious agent or toxin. "Reverse isolation" refers to protection of the assay device from spurious exogenous contamination, such as with a nucleic acid, that may cause false positives.

Waste chamber or "pack": is a cavity or chamber that serves as a receptacle for sequestering discharged sample, rinse solution, and waste reagents. Typically also includes a wicking material (see wick). Waste packs may also be sealed under an elastic isolation membrane sealingly attached to the body of the microfluidic device. This inner membrane expands as the bibulous material expands, thus enclosing the waste material. The cavity outside the isolation membrane is vented to atmosphere so that the waste material is contained and isolated. Waste packs may optionally contain dried or liquid sterilants.

Wick: is a bibulous material used to propulse fluid flow by capillary wetting in place of, or in concert with, microfluidic pumps. The bibulous core typically includes a fibrous web of natural or synthetic fibers, and also often includes certain absorbent gelling materials usually referred to as "hydrogels," "superabsorbent" or "hydrocolloid" materials. Materials include papers, sponges, diaper materials, Contec-Wipe, and others. Dessicants may also be used, such as calcium sulfate, calcium sulfate, silica gel, alone or in combination with bibulous materials.

Trap: a fluid trap with dam that further isolates a waste reservoir from a vent.

Vent: a pore intercommunicating between an internal cavity and the atmosphere. A "sanitary" or "isolation vent" also contains a filter element that is permeable to gas, but is hydrophobic and resists wetting. Optionally these filter elements have pore diameters of 0.45 microns or less. These filters function both in forward and reverse isolation. Filter elements of this type and construction may also be placed internally, for example to isolate a valve or bellows pump from the pneumatic manifold controlling it.

Test field: refers to the site in the microfluidic device-based assay where the assay endpoint is observed or measured, such as an optical window, and is optionally a detection chamber containing test pads.

"Conventional" is a term designating that which is known in the prior art to which this invention relates.

"About" and "generally" are broadening expressions of inexactitude, describing a condition of being "more or less," "approximately," or "almost" in the sense of "just about," where variation would be insignificant, obvious, or of equivalent utility or function, and further indicating the existence of obvious minor exceptions to a norm, rule or limit. For example, in various embodiments the foregoing terms refer to a quantity within 20%, 10%, 5%, 1% or 0.1% of the value which follows the term.

Herein, where a "means for a function" is described, it should be understood that the scope of the invention is not limited to the mode or modes illustrated in the drawings alone, but also encompasses all means for performing the function that are described in this specification, and all other means commonly known in the art at the time of filing. A "prior art means" encompasses all means for performing the function as are known to one skilled in the art at the time of filing, including the cumulative knowledge in the art cited herein by reference to a few examples.

A means for polymerizing, for example, may refer to various species of molecular machinery described as polymerases and their cofactors and substrates, for example reverse transcriptases and TAQ polymerase, and includes the cumulative knowledge of enzymology cited herein by reference to a few examples.

Means for Amplifying include thermocycling and isothermal means. The first thermocycling technique was the polymerase chain reaction (referred to as PCR) which is described in detail in U.S. Pat. Nos. 4,683,195, 4,683,202 and 4,800,159, Ausubel et al. Current Protocols in Molecular Biology, John Wiley and Sons, Baltimore, Md. (1989), and in Innis et al., ("PCR Protocols," Academic Press, Inc., San Diego Calif., 1990), the disclosures of which are incorporated herein by reference in their entirety. Polymerase chain reaction methodologies are well known in the art. Briefly, in PCR, two primer sequences are prepared that are complementary to regions on opposite complementary strands of a target sequence. An excess of deoxynucleoside triphosphates are added to a reaction mixture along with a DNA polymerase, e.g., Taq polymerase. If the target sequence is present in a sample, the primers will bind to the target and the polymerase will cause the primers to be extended along the marker sequence by adding on nucleotides. By raising and lowering the temperature of the reaction mixture, the extended primers will dissociate from the template to form reaction products, excess primers will bind to the template and to the reaction products and the process is repeated. By adding fluorescent intercalating agents, PCR products can be detected in real time.

One isothermal technique is LAMP (loop-mediated isothermal amplification of DNA) and is described in Notomi, T. et al. Nucl Acid Res 2000 28.

Strand Displacement Amplification (SDA) is another method of carrying out isothermal amplification of nucleic acids which involves multiple rounds of strand displacement and synthesis, i.e., nick translation (Walker et al. Nucleic Acids Research, 1992: 1691-1696, incorporated herein by reference). A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Another nucleic acid amplification technique is reverse transcription polymerase chain reaction (RT-PCR). First, complementary DNA (cDNA) is made from an RNA template, using a reverse transcriptase enzyme, and then PCR is performed on the resultant cDNA.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750, the disclosure of which is incorporated herein by reference in its entirety, describes a method similar to LCR for binding probe pairs to a target sequence.

QβReplicase, may also be used as still another amplification method in the present invention. In this method, a replicative sequence of RNA that has a region complementary to that of a target is added to a sample in the presence of an RNA polymerase. The polymerase will copy the replicative sequence that can then be detected.

Still further amplification methods, described in GB Application No. 2 202 328, and in PCT Application No. PCT/US89/01025, the disclosures of which are incorporated herein by reference in their entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989, Proc. Natl. Acad. Sci. U.S.A., 86: 1173; Gingeras et al., PCT Application WO 88/10315, the disclosures of which are incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNAs are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPO No. 329 822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase D, resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al. in PCT Application WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, M. A., In: "PCR Protocols: A Guide to Methods and Applications," Academic Press, N. Y., 1990; Ohara et al., 1989, Proc. Natl. Acad. Sci. U.S.A., 86: 5673-567, the disclosures of which are incorporated herein by reference in their entireties).

Methods based on ligation of two (or more) oligonucleotides in the presence of nucleic acid having the sequence of the resulting "di-oligonucleotide," thereby amplifying the di-oligonucleotide, may also be used in the amplification step of the present invention. Wu et al., (1989, Genomics 4: 560, incorporated herein by reference in its entirety).

Means for detecting: as used herein, refers to an apparatus for displaying an endpoint, i.e., the result of an assay, and may include a detection channel and test pads, and a means for evaluation of a detection endpoint. Detection endpoints are evaluated by an observer visually in a test field, or by a machine equipped with a spectrophotometer, fluorometer, luminometer, photomultiplier tube, photodiode, nephlometer, photon counter, voltmeter, ammeter, pH meter, capacitative sensor, radio-frequency transmitter, magnetoresistometer, or Hall-effect device. Magnetic particles, beads and microspheres having or impregnated color or having a higher diffraction index may be used to facilitate visual or machine-enhanced detection of an assay endpoint. Magnifying lenses in the cover plate, optical filters, colored fluids and labeling may be used to improve detection and interpretation of assay results. Means for detection of magnetic particles, beads and microspheres may also include embedded or coated "labels" or "tags" such as, but not limited to, dyes such as chromophores and fluorophores; radio frequency tags, plasmon resonance, spintronic, radiolabel, Raman scattering, chemoluminescence, or inductive moment as are known in the prior art. Colloidal particles with unique chromogenic signatures depending on their self-association are also anticipated to provide detectable endpoints. QDots, such as CdSe coated with ZnS, decorated on magnetic beads, or amalgamations of QDots and paramagnetic $Fe_3O_4$ microparticles, optionally in a sol gel microparticulate matrix or prepared in a reverse emulsion, are a convenient method of improving the sensitivity of an assay of the present invention, thereby permitting smaller test pads and larger arrays. Fluorescence quenching detection endpoints are also anticipated. A variety of substrate and product chromophores associated with enzyme-linked immunoassays are also well known in the art and provide a means for amplifying a detection signal so as to improve the sensitivity of the assay. Detection systems are optionally qualitative, quantitative or semi-quantitative. Visual detection is preferred for its simplicity, however detection means can involve visual detection, machine detection, manual detection or automated detection.

Means for heating and cooling: A number of means for thermocycling a liquid filled chamber have been described in the prior art. These prior art means include convective and conductive heating elements such as electroresistors, hot air, lasers, infrared radiation, Joule heating, TEC or Peltier devices, heat pumps, endothermic reactants, and the like, generally in conjunction with a heat sink for dissipating heat during chill-down parts of the cycle. Heating means may also include heating by the motion of magnetic beads driven by a high frequency magnetic field.

Heating and cooling devices for thermocycling fall into two categories: ramped and fixed temperature. Fixed temperature devices maintain a relatively constant temperature in a reaction, and at least two reaction chambers are needed for thermocycling. Ramped heating devices will vary the temperature between at least two set points, and therefore only one reaction chamber is required for thermocycling. Combinations of heating elements are possible. Peltier devices may be used for both fixed temperature and ramped applications. Water baths are not well adapted to ramped temperature control for thermocycling.

Generally, heating and cooling means interface with a fluidics member so as to effect heat exchange with the liquid contents. For PCR, the relevant elements forming the microfluidic channels or chambers where heat exchange takes place are termed as part of the "PCR fluidics and thermal interface" assembly.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

2. Preparation of Nucleic Acid-containing Samples

The present inventors have surprisingly found that the combined use of a clay mineral and an alkaline solution can be used to prepare complex biological samples for nucleic acid analysis. In some embodiments, these reagents can be advantageously used to prepare a common sample for the detection of both DNA and RNA target molecules in a microfluidic device. The method of the invention offers improvements over known sample preparation methods in that the present method does not require further purification or isolation of the nucleic acids prior to detection by amplification, for example. Although not required, embodiments which include optional purification and/or isolation steps prior to detection by amplification are also contemplated. The nucleic acid samples prepared under the present invention are essentially free of nuclease activity and are superior substrates for modifying enzymes. The sample preparation methods performed by the microfluidic devices disclosed herein are particularly advantageous in the preparation of blood or serum samples for the detection of both DNA and RNA viruses.

Figure 6:
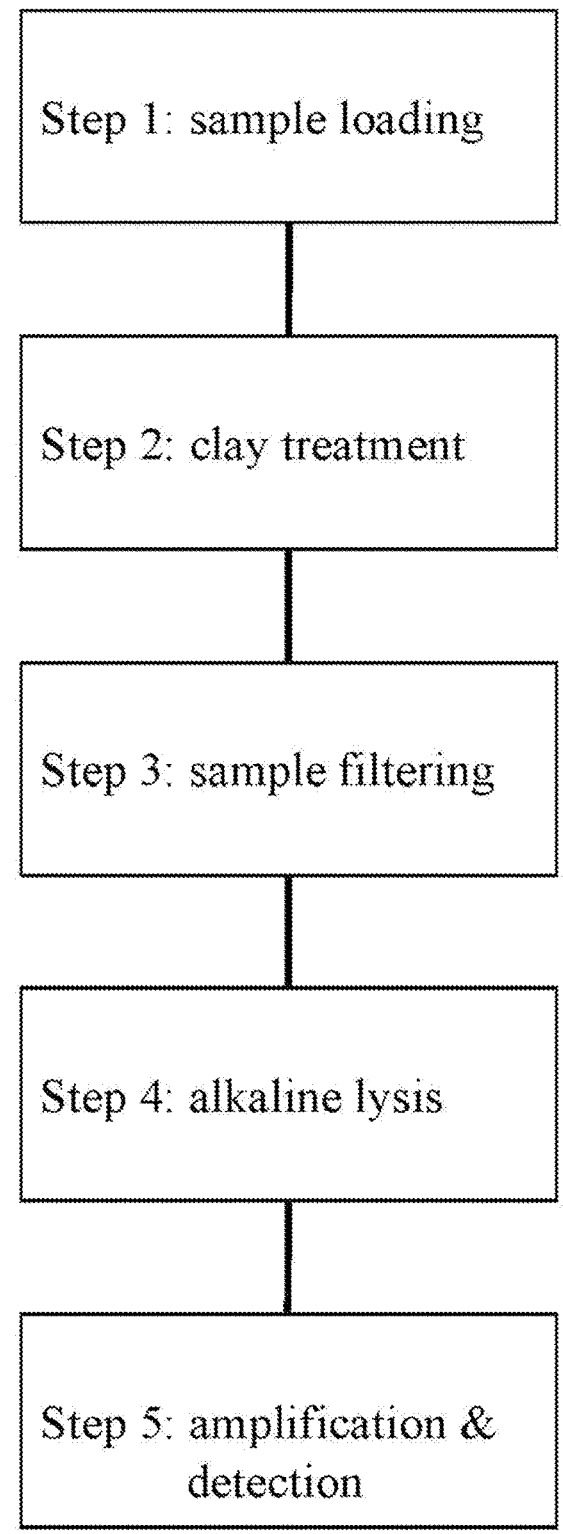
FIG. 6 is a step-by-step guide of examples of processes that may be undertaken in the device of the present invention.

In one embodiment, the present invention relates to a microfluidic device for preparing a nucleic acid-containing sample for diagnostic analysis of target nucleic acids. Accordingly, in various embodiments, a test sample loaded into the device undergoes several steps, as shown in FIG. 6. The sample preparation method comprises contacting the biological sample solution with a clay mineral, mixing the biological sample solution and the clay mineral until the clay mineral is evenly dispersed in the biological sample solution, filtering the mixed sample to substantially remove the clay mineral from the test sample, and contacting the test sample with an alkaline solution at a pH suitable for lysis of cell and viral particles to form a nucleic acid solution. In further embodiments the methods include performing a molecular assay based on, for example, nucleic acid amplification of the nucleic acid solution. The method may comprise an additional, optional step of contacting the nucleic acid solution with an acidic solution suitable for neutralizing the pH of the nucleic acid solution after sample lysis and prior to amplification. In some exemplary embodiments, all of the reagents necessary for performing this means of nucleic acid sample preparation are pre-loaded onto the microfluidic devices of the present invention. It should be noted that FIG. 6 is provided for purpose of illustration of one embodiment of the present invention and all steps illustrated in FIG. 6 are not required in all embodiments and further non-illustrated steps may also be included.

The clay mineral within the meaning of the invention may be any single clay mineral or a mixture of different clay minerals. Suitable clay minerals for use in the embodiments disclosed herein include, but are not limited to clays of the following groups: the kaolinite group or (e.g., kaolinite, dickite, nacrite, halloysite, hisingerite); the montmorillonite/smectite group (e.g., beidellite, pyrophyllitevermiculite, sauconite, saponite, nontronite and montmorillonite); talc is often, but not always, placed in this group); the illite (or the clay-mica) group (e.g., muscovite, illite); and the chlorite group (e.g., amesite, baileychlore, chamosite, clinochlore, kaemmererite, cookeite, corundophilite, daphnite, delessite, gonyerite, nimite, odinite, orthochamosite, penninite, pannantite, rhipidolite, prochlore, sudoite, thuringite). Other clay minerals suitable in the present invention include, but are not limited to, albites, phillipsites, analcites, and gibbsites.

Clay minerals are also defined in the art by their atomic structures. Clay minerals formed of a series of 1 tetrahedron and 1 octahedron layer each are referred to as two-layer clay minerals, 1:1 minerals, or as 7 Å clay minerals after the spacing (referred to in the specialist terminology as base spacing), of the tetrahedron layers. This group includes, for example, kaolinite, halloysite, dickite and nakrite. Clay minerals from formations of 1 octahedron and 2 tetrahedron layers are referred to as three-layer, 10 Å minerals, or 2:1 minerals. This group includes, for example, illite and the smectites, glauconite and vermiculite. Montmorillonite is the main representative of the smectite group and the main component of bentonite. In practice bentonite, smectite and montmorillonite are commonly used as synonyms for multilayer silicates. If a further independent octahedron layer is incorporated between the three-layer formations, four-layer, or 14 Å minerals, are produced. A representative of this group is the chlorites. A special clay mineral group is represented by interbedded minerals. Between the layer packages, ions and water molecules can, for example, become embedded. This may lead to an expansion of the layer spacings (swelling), which is commonly observed in the smectites. Any of the clay minerals and clay mineral structures described herein is suitable for the practice of the present invention.

Various types of clay minerals as described herein are available commercially from companies such as Thiele Kaolin Co. (Sandersville, Ga.), Imerys (Roswell, Ga.), Dry Branch Kaolin Co. (Dry Branch, Ga.), Millennium Inorganic Chemicals (Baltimore, Md.), and Minerals Technology Inc. (Specialty Minerals, Bethlehem, Pa.) BYK-Chemie GmbH (Wesel, Germany), Sigma-Aldritch (St. Louis, Mo.), American Colloid Company (Arlington Heights, Ill.).

According to a particular embodiment of the invention, montmorillonite or bentonite is used. Montmorillonite is available under the tradename, MK10. In practice, bentonite, montmorillonite, and smectite are commonly used as synonyms for multi-layer silicates. Montmorillonite is the pure clay mineral. Bentonite is an impure mixture of mostly montmorillonite that may also contain illite and kaolinite. The main types of bentonite are defined by the dominant cation between the sheets of clay: potassium, aluminum, sodium, or calcium. As used here, bentonite contains sodium, but all types of bentonite clays are suitable for the practice of the present invention. According to another embodiment, halloysite is used as a clay mineral. According to yet another embodiment of the invention, Fuller's earth is used as a clay mineral. Fuller's Earth is known in the art as a complex mixture that includes montmorillonites, kaolinites and attapulgites, as well as other minerals like calcite and quartz. According to another embodiment of the invention, the synthetic clay laponite (BYK-Chemie GmbH (Wesel, Germany), is used as a clay mineral. Whenever mention is made of "a clay mineral" herein, this term is also intended to include mixtures of the aforementioned clays.

According to embodiments of the present invention, the test sample is in the form of a suspension solution. The method used to suspend a given biological sample in solution will depend upon its nature. Some liquid samples require no further suspension, for example, blood products or urine. In some cases, a liquid solution will require dilution with phosphate-buffered saline (PBS) or similar diluent. Many forms of animal tissue will require more vigorous treatment before being suspended, such as freezing and/or pulverizing, or by homogenization with a blender or other mechanical mixing device. In some embodiments, a suspension solution is an aqueous solution, for example an aqueous solution comprising a buffer. In one embodiment, the test sample comprises an acetate buffer at around pH 6.0

The clay mineral may be pre-loaded into the microfluidic device of the invention in dry form and become hydrated by suspension in the test sample. Alternatively, the clay mineral may be pre-loaded into the microfluidic device in a hydrated form. In one embodiment of the invention, the clay mineral is pre-hydrated in an acetate buffer at around pH 6.0.

In one embodiment of the invention, the clay mineral is pre-loaded into the microfluidic device such that upon addition of the test sample, the clay is suspended at a concentration of around 20 mg/mL. Other suitable concentrations are contemplated, such as from around 1 mg/mL, 5 mg/mL, 10 mg/mL, 15 mg/mL, 25 mg/mL, 30 mg/mL, 40 mg/mL, 50 mg/mL, 60 mg/mL, 75 mg/mL, 90 mg/mL, 100 mg/mL, 125 mg/mL, 150 mg/mL and up to about 160 mg/mL. It will be appreciated that the amount of clay mineral added to the biological sample solution will be an amount sufficient to prevent degradation of target nucleic acids and interference with downstream molecular analyses.

As used herein, alkaline solution, alkaline buffer, and alkaline lysis solution are used interchangably. The alkaline lysis solution of the present invention comprises a base. Preferably the base is sufficiently strong to raise the pH of the test sample to a level wherein the structures of the cell membranes and/or viral particles are disrupted (i.e. "lysed") and the nucleic acids of interest are released in undamaged form, (i.e. "intact"). In one embodiment, the base is potassium hydroxide (KOH). In other embodiments, the base is sodium hydroxide (NaOH) or lithium hydroxide (LiOH). Alkaline solutions or buffers are prepared by mixing the alkaline base in a suitable solvent, such as water at a concentration of around 1M. In one embodiment, the alkaline solution or buffer is added at a final concentration of around 0.1M. It will be appreciated by one of skill in the art that other suitable concentrations may be used in the present invention to achieve effective treatment of the test sample.

The microfluidic devices of the present invention may also include an optional pre-loaded neutralization buffer. Several suitable acids may be used as the optional acidic solution or buffer of the invention. Exemplary acids include hydrochloric acid (HCl) and acetic acid ($C_2H_4O_2$). Acidic solutions or buffers are prepared by mixing the acid with water at a concentration of around 1M. For the optional neutralization step of the present invention, the acidic solution or buffer is added at a concentration sufficient to neutralize the alkaline lysis buffer to around a physiologic pH, such as around pH 7.2. In one embodiment, the acidic buffer or solution is added at a final concentration of around 0.1M.

In certain embodiments, nucleic acid-containing test samples prepared in accordance to the methods of the present invention are used directly in downstream amplification procedures without any further purification or isolation steps. A single nucleic acid-containing test sample prepared as disclosed herein may be used to detect both DNA and RNA target molecules.

3. Microfluidic Devices for Preparation and Analysis of Nucleic Acid-containing Test Samples Embodiments of the present invention are generally directed to microfluidic devices for preparation and optional analysis of samples containing, or suspected of containing, a nucleic acid of interest ("a sample" or "test sample"). In one embodiment, the invention provides a microfluidic device comprising a microfluidic channel having a first end and a second end and a sample inlet fluidly connected to the first end of the microfluidic channel. Connected to the second end of the microfluidic channel is a clay treatment chamber that may optionally be preloaded with a clay mineral or mixture of clay minerals as described herein. Microfluidic device of this embodiment are useful for treatment a sample to prepare it for optional nucleic acid analyses. These nucleic acid analyses may be either performed on the microfluidic device or the sample may be removed after treatment in the clay treatment chamber and the subsequent operations performed "off card."

In further embodiments of the foregoing, the sample inlet is designed to allow a liquid test sample to be loaded into the device. It may be suitable, for example, for injection of a sample through a syringe or a micropipette. The device may also comprise an optional composite membrane interposed between the sample inlet and first end of the microfluidic channel. In one embodiment of the invention, a composite membrane may be used when the test sample is a whole blood sample. As used herein, the term "membrane" refers to any planar material with a Z-dimension, including filters, which are porous membranes. Composite membranes of the invention are further described in FIG. 5 below.

In other further embodiments, the microfluidic devices are configured to lyse a clay-treated sample. Accordingly, in some embodiments the device further comprises a sample lysis chamber fluidly connected to, and downstream of, the clay treatment chamber. The lysis chamber may optionally be preloaded with an alkaline buffer or solution suitable for lysing cells or viral particles present in the sample to release target nucleic acids. The alkaline buffer or solution may be any suitable alkaline buffer, for example KOH, NaOH, or LiOH or other appropriate alkaline buffer. The alkaline buffer may be provided as a liquid, stored in a blister pack, and released during operation, or provided in dry form, each alternative as further described herein.

If desired, the device may further comprise a separate sample neutralization chamber downstream of a sample lysis chamber that contains the buffers or reagents necessary to neutralize the extracted sample, as described herein. In certain embodiments, the neutralization buffer or reagent is selected from HCl or acetic acid. Similarly, the neutralization buffer may be provided as a liquid, stored in a blister pack, and released during operation or provided in dry form, each alternative as further described herein.

Optionally, the device also comprises a nucleic acid amplification well downstream of a nucleic acid lysing chamber. When present, such nucleic acid amplification wells may contain all of the necessary reagents for such, as further described here. In various embodiments, the nucleic acid amplification chamber also serves as a detection chamber (i.e., amplification and detection are performed in the same chamber). Alternatively, the devices may include one or more separate detection chambers where the amplified product from the amplification chamber is detected.

Accordingly, in one embodiment the invention provides a microfluidic device comprising:

a microfluidic channel having a first end and a second end;

a sample inlet fluidly connected to the first end of the microfluidic channel and configured for receiving a test sample;

a clay treatment chamber fluidly connected to said microfluidic channel, wherein said clay treatment chamber contains a clay mineral reagent;

a sample lysis chamber fluidly connected to said clay treatment chamber, wherein said sample lysis chamber contains an alkaline solution;

one or more sample nucleic acid amplification or detection wells, or combinations thereof, fluidly connected to said sample lysis chamber; and and one or more sample outlets.

The devices find utility in any number of applications, including preparing and/or analyzing nucleic acids in a test sample.

In certain embodiments, the sample is a biological sample (e.g., blood, tissue or other sample containing cells). The sample may be provided in various forms, for example as a solution, as a suspension or combinations thereof. In various embodiments the sample is a biological sample solution.

The exact type of clay used in the devices is not particularly limited and can be selected from clays known to one of skill in the art, for example any of the specific clay minerals described herein. In some embodiments, the clay mineral comprises a kaolinite, smectite, or illite clay mineral. In different embodiments, the clay mineral comprises talc. In other embodiments, the clay mineral comprises halloysite. In more embodiments, the clay mineral comprises bentonite. In yet other embodiments, the clay mineral comprises a synthetic clay mineral, for example a laponite.

The alkaline solution is also not particularly limited provided the pH is greater than 7. In some embodiments, the alkaline solution comprises KOH, NaOH, or LiOH, or combinations thereof. In some embodiments, the alkaline solution comprises KOH. In other embodiments, the alkaline solution comprises NaOH. In different embodiments, the alkaline solution comprises LiOH. In various embodiments of the foregoing, the alkaline solution is an aqueous solution of any of the foregoing bases.

Alkaline solutions or buffers are prepared by mixing the alkaline base in a suitable solvent, such as water at a concentration of around 1M. In one embodiment, the alkaline solution or buffer is added at a final concentration of around 0.1M. It will be appreciated by one of skill in the art that other suitable concentrations may be used in the present invention to achieve effective treatment of the test sample.

Although not required, certain embodiments include an optional neutralization chamber downstream of the lysis chamber. Such optional neutralization chambers comprise solutions for neutralizing the alkaline lysis solution. The neutralizing solution will typically be acidic (i.e., pH less than 7). For example, in some embodiments, the optional acidic solution comprises HCl, $C_2H_4O_2$, or $H_2SO_4$. In some embodiments, the optional acidic solution comprises HCl. In other embodiments, the optional acidic solution comprises $C_2H_4O_2$. In still more embodiments, the optional acidic solution comprises $H_2SO_4$. The optional acidic solution may be provided in the form of an aqueous solution of any suitable acid, for example any of the foregoing acids.

For the optional neutralization chamber of the present invention, the acidic solution or buffer is present at a concentration sufficient to neutralize the alkaline lysis buffer to around a physiologic pH, such as around pH 7.2. In one embodiment, the acidic buffer or solution is present at a final concentration of around 0.1M.

Any sample which contains a nucleic acid of interest may be employed in the presently disclosed devices. In certain embodiments, the sample comprises one or more infectious agents. In certain of these embodiments, the one or more infectious agents are viral agents. In some embodiments, the sample comprises at least two viral agents. For example, in various embodiments, the sample comprises a DNA virus and an RNA virus. In some embodiments, the DNA virus is HBV, and in other embodiments the RNA virus is HCV or HIV.

In some different embodiments, the device is configured for analysis of a sample selected from blood, plasma, serum, urine, saliva, sputum, respiratory lavage, tears, and tissue swabs. In more specific embodiments, the sample is selected from blood, plasma, and serum.

In some other embodiments, the device further comprises an on-device pump fluidly connected to the second end of the microfluidic channel.

In yet other embodiments, the device further comprises a composite membrane interposed between the sample inlet and the first end of the microfluidic channel, wherein the composite membrane is capable of removing selected particles from blood. In some embodiments, the composite membrane comprises a material that activates blood coagulation. In other embodiments, the composite membrane comprises a glass filter.

In various different embodiments, the device is configured for performing a nucleic acid amplification step, for example a nucleic acid amplification step selected from PCR, RT-PCR, qPCR, and qRT-PCR.

Embodiments of the present invention are better understood in reference to the following description of the figures. It should be noted that although the figures depict embodiments of the microfluidic device which include a clay treatment chamber, lysis chamber and amplification chamber, the invention is not so limited, and embodiments are provided which include a clay treatment chamber with the lysis or amplification chamber or a clay treatment chamber and lysis chamber without the amplification chamber.

FIG. 1 is a schematic view of device 110 illustrating a first embodiment of the invention. As shown in FIG. 1, a microfluidic device 110 comprises a microfluidic channel 120 having a first end 122 and a second end 124. As illustrated, device 110 is in the form of a cartridge, however, the form of device 110 is not essential to the present invention and persons of ordinary skill in the art can readily select a suitable form for a given application. The microfluidic devices of the present invention, such as device 110, may be constructed from a material, such as plastic, mylar or latex, using a method such as injection molding or lamination as described herein.

As further shown in FIG. 1, device 110 comprises a sample inlet 130 fluidly connected to first end 122 of microfluidic channel 120 for receiving a test sample. The sample inlet is designed to allow a liquid test sample to be loaded into the device. It may be suitable, for example, for injection of a sample through a syringe or a micropipette. Device 110 may also comprise an optional composite membrane interposed between sample inlet 130 and first end 122 of microfluidic channel 120. In one embodiment of the invention, a composite membrane may be used when the test sample is a whole blood sample. As used herein, the term "membrane" refers to any planar material with a Z-dimension, including filters, which are porous membranes. Composite membranes of the invention are further described in FIG. 5 below.

For nucleic acid sample preparation, device 110 comprises a clay treatment chamber 150 that is preloaded with a clay mineral or mixture of clay minerals as described herein. The clay mineral may be provided as a liquid (e.g., suspensions in appropriate solvent or buffer), stored in a blister pack, and released during operation. Alternatively, it may be provided in dry form, as further described herein. The clay treatment chamber further comprises a filtration unit. This unit may either be upstream of, or integrally formed with, the chamber downstream of the clay treatment chamber. The filtration unit may comprise, for example, a hollow filter with a pore size of 0.45 μM. Device 110 further comprises a sample lysis chamber 160 that may be preloaded with an alkaline buffer or solution suitable for lysing cells or viral particles present in the test sample to release target nucleic acids. The alkaline buffer or solution may be any one of KOH, NaOH, or LiOH or other appropriate alkaline buffer. The alkaline buffer may be provided as a liquid, stored in a blister pack, and released during operation, or provided in dry form, each alternative as further described herein. If desired, device 110 may further comprise a separate sample neutralization chamber downstream of sample lysis chamber that contains the buffers or reagents necessary to neutralize the extracted sample, as described herein. In certain embodiments, the neutralization buffer or reagent is selected from HCl or acetic acid. Similarly, the neutralization buffer may be provided as a liquid, stored in a blister pack, and released during operation or provided in dry form, each alternative as further described herein. Device 110 also comprises nucleic acid amplification well 170 in which any of the molecular assays described herein may be performed and which may contain all of the necessary reagents for such, as further described here. In various embodiments, the nucleic acid amplification chamber also serves as a detection chamber (i.e., amplification and detection are performed in the same chamber). Alternatively, the devices may include one or more separate detection chambers where the amplified product from the amplification chamber is detected. Outlet well 180 provides the user with access to the amplified product(s) and also functions as a vent.

In various embodiments, the present invention comprises these three chambers, namely the clay treatment chamber, the sample lysis chamber, and the nucleic amplification chamber, arranged sequentially in this order. The clay treatment chamber is typically positioned upstream of the sample lysis chamber. Each chamber has two ends and these two ends are nominally given the labels upper and a lower end. The upper ends of each chamber may be connected to a first variable position valve while the lower ends are connected to a second variable position valve. Valves may be actuated by external ("of-card") means, such as a pump that applies positive or negative pressure as further described herein. These optional valves are shown as 123*a-d* in FIG. 1.

In various embodiments, methods for use of the microfluidic devices are provided. During operation of one embodiment of the invention, a test sample, for example a clinically obtained blood sample, is placed into sample inlet 130. Thereafter, the sample may, optionally, contact and an optional composite membrane. The sample is drawn into channel 120 by external means and enters clay treatment chamber 150. In clay treatment chamber 150, the sample is mixed with a clay mineral such that the clay becomes evenly dispersed in the sample as described herein. The sample exits clay treatment chamber through a filter, which retains a substantial portion of the clay material, particularly large clay aggregates. The sample then enters sample lysis chamber 160, where the sample is contacted with an alkaline solution to solubilize cellular and viral material contained therein and release target nucleic acids. Optionally, the sample may enter a downstream neutralization chamber where the pH of the sample is adjusted to the appropriate level as described herein. The lysed or "extracted" and nucleic acid-containing sample then enters nucleic acid amplification and detection chamber 170 where molecular analysis takes place by any of the methods disclosed herein. The user may gain access to the amplified product(s) through outlet well 180, which also functions as a vent.

Figure 2:
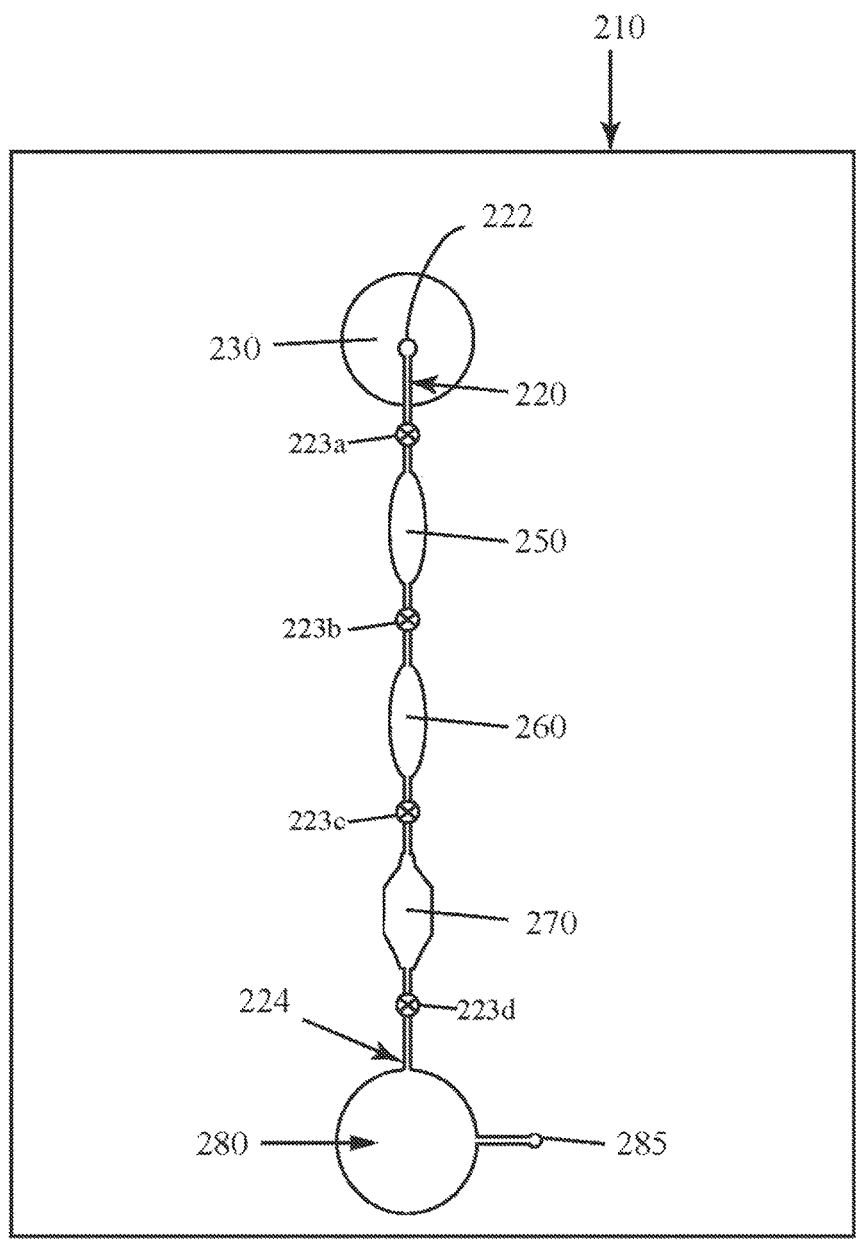
FIG. 2 is a schematic view illustrating the operation of a second embodiment of a microfluidic device in accordance with aspects of the present invention.

FIG. 2 is a schematic view of device 210 illustrating an alternative embodiment of the invention. As shown in FIG. 2, a microfluidic device 210 comprises a microfluidic channel 220 having a first end 222 and a second end 224. As illustrated, device 210 is in the form of a cartridge, however, the form of device 210 is not essential to the present invention and persons of ordinary skill in the art can readily select a suitable form for a given application. The microfluidic devices of the present invention, such as device 210, may be constructed from a material, such as plastic, mylar or latex, using a method such as injection molding or lamination as described herein.

As further shown in FIG. 2, device 210 comprises a sample inlet 230 fluidly connected to first end 222 of microfluidic channel 220 for receiving a test sample. The sample inlet is designed to allow a liquid test sample to be loaded into the device. It may be suitable, for example, for injection of a sample through a syringe or a micropipette. Device 210 may also comprise an optional composite membrane interposed between sample inlet 230 and first end 222 of microfluidic channel 220. In one embodiment of the invention, a composite membrane may be used when the test sample is a whole blood sample. As used herein, the term "membrane" refers to any planar material with a Z-dimension, including filters, which are porous membranes. Composite membranes of the invention are further described in FIG. 5 below.

For nucleic acid sample preparation, device 210 comprises a clay treatment chamber 250 that may be preloaded with a clay mineral or mixture of clay minerals as described herein. The clay mineral may be provided as a liquid (e.g., suspension), stored in a blister pack, and released during operation. Alternatively it may be provided in dry form, as further described herein. The clay treatment chamber further comprises a filtration unit. This unit may either be upstream of, or integrally formed with, the chamber downstream of the clay treatment chamber. The filtration unit may comprise, for example, a hollow filter with a pore size of 0.45 µM. Device 210 further comprises a sample lysis chamber 260 that is preloaded with an alkaline buffer or solution suitable for lysing cells or viral particles present in the test sample to release target nucleic acids. The alkaline buffer or solution may be any suitable alkaline buffer, such as KOH, NaOH, or LiOH. The alkaline buffer may be provided as a liquid, stored in a blister pack, and released during operation, or provided in dry form, each alternative as further described herein.

If desired, device 210 may further comprise a separate sample neutralization chamber downstream of sample lysis chamber that contains the buffers or reagents necessary to neutralize the extracted sample, as described herein. In certain embodiments, the neutralization buffer or reagent is selected from HCl or acetic acid. Similarly, the neutralization buffer may be provided as a liquid, stored in a blister pack, and released during operation or provided in dry form, each alternative as further described herein. Device 210 also comprises nucleic acid amplification well 270 in which any of the molecular assays described herein may be performed and which may contain all of the necessary reagents for such, as further described here. In various embodiments, the nucleic acid amplification chamber is also a detection chamber (i.e., amplification and detection are performed in the same chamber). Alternatively, the devices may include one or more separate detection chambers where the amplified product from the amplification chamber is detected. A finger pump 280 having a sample collection port 285 is fluidly connected to the second end 224 of microfluidic channel 220.

In some embodiments, the present invention comprises these three chambers, namely the clay treatment chamber, the sample lysis chamber, and the nucleic amplification chamber, arranged sequentially in this order. Each chamber has two ends and these two ends are nominally given the labels upper and a lower end. The upper ends of each chamber may be connected to a first variable position valve while the lower ends are connected to a second variable position valve. Valves may be actuated by external ("off-card") means, such as a pump that applies positive or negative pressure as further described herein. Optional valves 223a-d are shown in FIG. 2.

During operation of one embodiment of the methods of the invention, a test sample, for example a clinically obtained blood sample, is placed into sample inlet 230. Thereafter, the sample may be contacted by an optional composite membrane. Finger pump 280 is depressed, either manually by a user or mechanically by an external device. Upon release of finger pump 280, negative fluid pressure is formed in microfluidic channel 220 and the test sample is drawn into the channel and enters clay treatment chamber 250. In clay treatment chamber 250, the sample is mixed with a clay mineral such that the clay becomes evenly dispersed in the sample as described herein. The sample exits clay treatment chamber through a filter, which retains a substantial portion of the clay material, particularly large clay aggregates. The sample then enters sample lysis chamber 260, where the sample is contacted with an alkaline solution to solubilize cellular and viral material contained therein and release target nucleic acids, as described above. Optionally, the sample may enter a downstream neutralization chamber where the pH of the sample is adjusted to the appropriate level as described herein. The lysed or "extracted" and nucleic acid-containing sample then enters nucleic acid amplification and detection chamber 270 where molecular analysis takes place by any of the methods disclosed herein. The user may gain access to the amplified product(s) through outlet well 285, which also functions as a vent.

Figure 3:
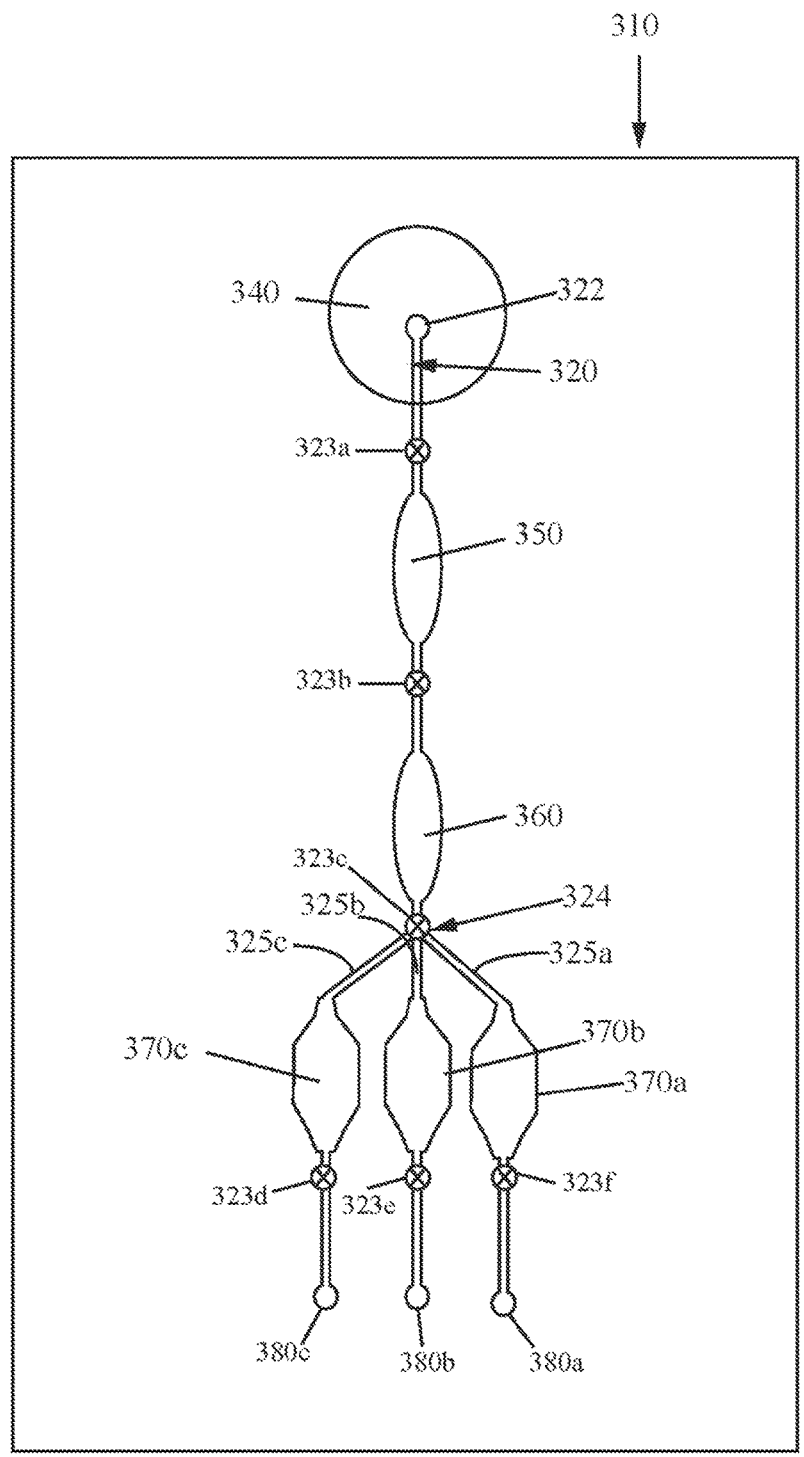
FIG. 3 is a schematic view illustrating the operation of a third embodiment of a microfluidic device in accordance with aspects of the present invention.

FIG. 3 is a schematic view of device 310 illustrating yet another embodiment of the invention. As shown in FIG. 3, a microfluidic device 310 comprises a microfluidic channel 320 having a first end 322 and a second end 324. As illustrated, device 310 is in the form of a cartridge, however, the form of device 310 is not essential to the present invention and persons of ordinary skill in the art can readily select a suitable form for a given application. The microfluidic devices of the present invention, such as device 310, may be constructed from a material, such as plastic, mylar or latex, using a method such as injection molding or lamination as described herein.

As further shown in FIG. 3, device 310 comprises a sample inlet 330 fluidly connected to first end 322 of microfluidic channel 320 for receiving a test sample. The sample inlet is designed to allow a liquid test sample to be loaded into the device. It may be suitable, for example, for injection of a sample through a syringe or a micropipette. Device 310 may also comprise an optional composite membrane interposed between sample inlet 330 and first end 322 of microfluidic channel 320. In one embodiment of the invention, a composite membrane may be used when the test sample is a whole blood sample. As used herein, the term "membrane" refers to any planar material with a Z-dimension, including filters, which are porous membranes. Composite membranes of the invention are further described in FIG. 5 below.

For nucleic acid sample preparation, device 310 comprises a clay treatment chamber 350 that may be preloaded with a clay mineral or mixture of clay minerals as described herein. The clay mineral may be provided as a liquid (e.g., suspension), stored in a blister pack, and released during operation. Alternatively, it may be provided in dry form, as further described herein. The clay treatment chamber further comprises a filtration unit. This unit may either be upstream of, or integrally formed with, the chamber downstream of the clay treatment chamber. The filtration unit may comprise, for example, a hollow filter with a pore size of 0.45 µM. Device 310 further comprises a sample lysis chamber 360 that is preloaded with an alkaline buffer or solution suitable for lysing cells or viral particles present in the test sample to release target nucleic acids. The alkaline buffer or solution may be any suitable alkaline buffer such as KOH, NaOH, or LiOH. The alkaline buffer may be provided as a liquid, stored in a blister pack, and released during operation, or provided in dry form, each alternative as further described herein.

If desired, device 310 may further comprise a separate sample neutralization chamber downstream of the sample lysis chamber that contains the buffers or reagents necessary to neutralize the extracted sample, as described herein. In certain embodiments, the neutralization buffer or reagent is selected from HCl or acetic acid. Similarly, the neutralization buffer may be provided as a liquid, stored in a blister pack, and released during operation or provided in dry form, each alternative as further described herein. Device 310 also comprises nucleic acid amplification chambers 370a, 370b, and 370c in which any of the molecular assays described herein may be performed and which may contain all of the necessary reagents for such, as further described here. In various embodiments, the nucleic acid amplification chambers are also detection chambers (i.e., amplification and detection are performed in the same chamber). Alternatively, the devices may include one or more separate detection chambers where the amplified product from the amplification chambers is detected. Although three amplification and detection chambers are depicted in this embodiment, fewer or greater numbers of amplification and detection chambers are suitable for practice of the present invention. Outlet wells 380a, 380b, and 380c provide the user with access to the amplified product(s) and also functions as a vent.

In some embodiments, the present invention comprises these five chambers, namely the clay treatment chamber, the sample lysis chamber, and the nucleic amplification chambers, which the clay treatment, lysis and amplification chambers are arranged in sequence in this order. Each chamber has two ends and these two ends are nominally given the labels upper and a lower end. The upper ends of each chamber may be connected to a first variable position valve while the lower ends are connected to a second variable position valve. Valves 323a-f may be actuated by external ("of-card") means, such as a pump that applies positive or negative pressure as further described herein.

During operation of one embodiment of the methods of the invention, a test sample, for example a clinically obtained blood sample, is placed into sample inlet 330. Thereafter, it may optionally, contact an optional composite membrane. The sample is drawn into channel 320 by external means and enters clay treatment chamber 350. In clay treatment chamber 350, the sample is mixed with a clay mineral such that the clay becomes evenly dispersed in the sample as described herein. The sample exits clay treatment chamber through a filter, which retains a substantial portion of the clay material, particularly large clay aggregates. The sample then enters sample lysis chamber 360, where the sample is contacted with an alkaline solution to solubilize cellular and viral material contained therein and release target nucleic acids. Optionally, the sample may enter a downstream neutralization chamber where the pH of the sample is adjusted to the appropriate level as described herein. The lysed or "extracted" sample containing target nucleic acids then is split into three samples, each of which enters one of three separate downstream channels 325a, 325b, or 325c. Downstream channels 325a, 325b, and 325c each lead to separate nucleic acid amplification and detection wells, 370a, 370b, and 370c for performing separate molecular assays. Outlet wells 380a, 380b, and 380c provides the user with access to the amplified products.

Figure 4:
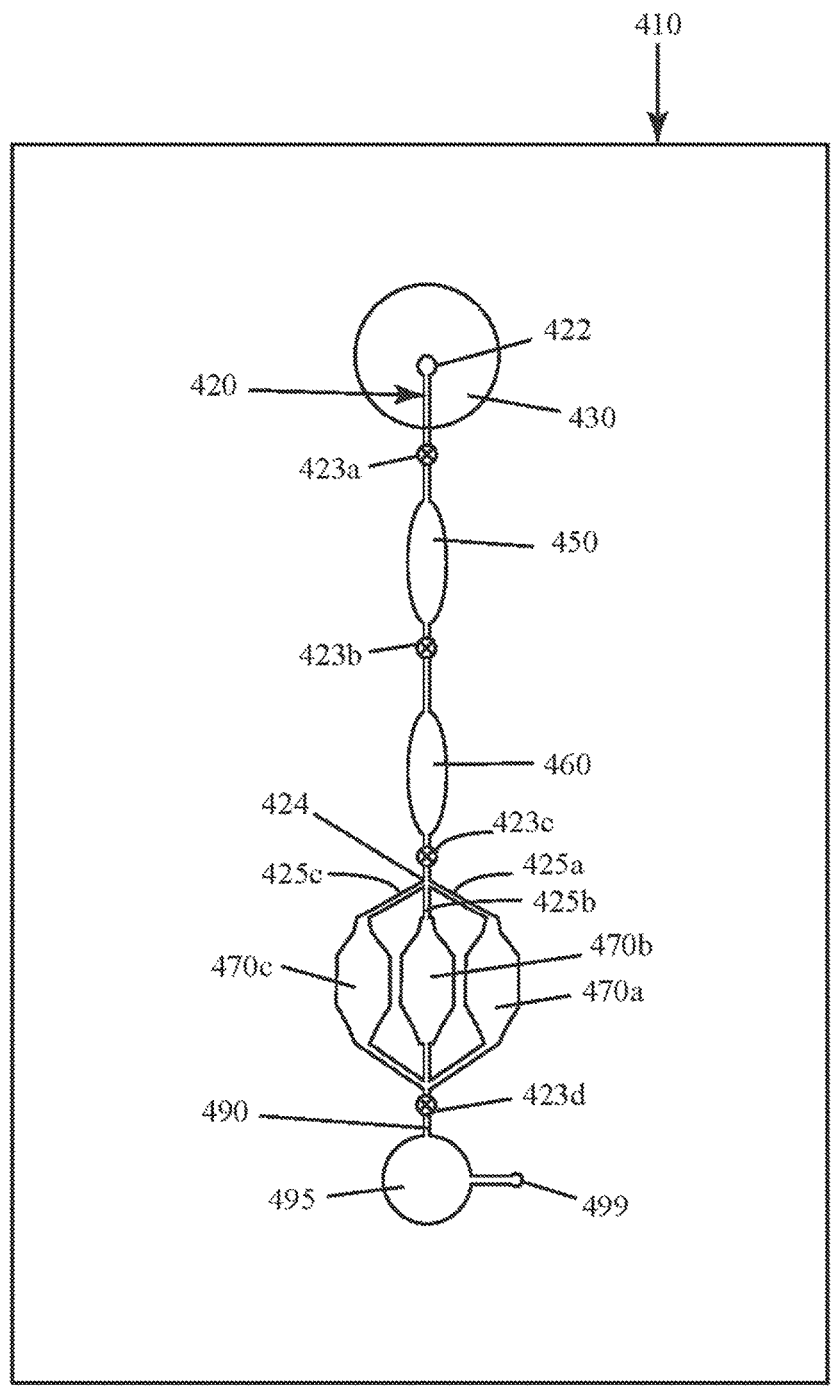
FIG. 4 is a schematic view illustrating the operation of a fourth embodiment of a microfluidic device in accordance with aspects of the present invention.

FIG. 4 is a schematic view of device 410 illustrating yet another embodiment of the invention. As shown in FIG. 4, a microfluidic device 410 comprises a microfluidic channel 420 having a first end 422 and a second end 490. As illustrated, device 410 is in the form of a cartridge, however, the form of device 410 is not essential to the present invention and persons of ordinary skill in the art can readily select a suitable form for a given application. The microfluidic devices of the present invention, such as device 410, may be constructed from a material, such as plastic, mylar or latex, using a method such as injection molding or lamination as described herein.

As further shown in FIG. 4, device 410 comprises a sample inlet 430 fluidly connected to first end 422 of microfluidic channel 420 for receiving a test sample. The sample inlet is designed to allow a liquid test sample to be loaded into the device. It may be suitable, for example, for injection of a sample through a syringe or a micropipette. Device 410 may also comprise an optional composite membrane interposed between sample inlet 430 and first end 422 of microfluidic channel 420. In one embodiment of the invention, a composite membrane may be used when the test sample is a whole blood sample. As used herein, the term "membrane" refers to any planar material with a Z-dimension, including filters, which are porous membranes. Composite membranes of the invention are further described in FIG. 5 below.

For nucleic acid sample preparation, device 410 comprises a clay treatment chamber 450 that may be preloaded with a clay mineral or mixture of clay minerals as described herein. The clay mineral may be provided as a liquid (e.g., suspension), stored in a blister pack, and released during operation. Alternatively, it may be provided in dry form, as further described herein. The clay treatment chamber further comprises a filtration unit. This unit may either be upstream of, or integrally formed with, the chamber downstream of the clay treatment chamber. The filtration unit may comprise, for example, a hollow filter with a pore size of 0.45 µM. Device 410 further comprises a sample lysis chamber 460 that is preloaded with an alkaline buffer or solution suitable for lysing cells or viral particles present in the test sample to release target nucleic acids. The alkaline buffer or solution may be any suitable buffer, such as KOH, NaOH, or LiOH. The alkaline buffer may be provided as a liquid, stored in a blister pack, and released during operation or provided in dry form, each alternative as further described herein.

If desired, device 410 may further comprise a separate sample neutralization chamber downstream of sample lysis chamber that contains the buffers or reagents necessary to neutralize the extracted sample, as described herein. In certain embodiments, the neutralization buffer or reagent is selected from HCl or acetic acid. Similarly, the neutralization buffer may be provided as a liquid, stored in a blister pack, and released during operation, or provided in dry form, each alternative as further described herein. Device 410 also comprises nucleic acid amplification chambers 470a, 470b, and 470c in which any of the molecular assays described herein may be performed and contain all of the necessary reagents for such, as further described here. In various embodiments, the nucleic acid amplification chambers are also detection chambers (i.e., amplification and detection are performed in the same chamber). Alternatively, the devices may include one or more separate detection chambers where the amplified product from the amplification chambers is detected. Although three amplification and detection chambers are depicted in this embodiment, fewer or greater numbers of amplification and detection chambers are suitable for practice of the present invention. A finger pump 495 having a sample collection port 499 is fluidly connected to the second end 490 of microfluidic channel 420.

In some embodiments, the present invention comprises these five chambers, namely the clay treatment chamber, the sample lysis chamber, and the nucleic amplification chambers, which the clay treatment, lysis and amplification chambers are arranged in sequence in this order. Each chamber has two ends and these two ends are nominally given the labels upper and a lower end. The upper ends of each chamber may be connected to a first variable position valve while the lower ends are connected to a second variable position valve. Valves 423a-d may be actuated by external ("of-card") means, such as a pump that applies positive or negative pressure as further described herein.

During operation of one embodiment of the methods of the invention, a test sample, for example a clinically obtained blood sample, is placed into sample inlet 430. Thereafter, the sample may optionally contact an optional composite membrane. Finger pump 495 is depressed, either manually by a user or mechanically by an external device. Upon release of finger pump 495, negative fluid pressure is formed in microfluidic channel 420 and the test sample is drawn into the channel and enters clay treatment chamber 450. The sample exits clay treatment chamber through a filter, which retains a substantial portion of the clay material, particularly large clay aggregates. The sample then enters sample lysis chamber 460, where the sample is contacted with an alkaline solution to solubilize cellular and viral material contained therein and release target nucleic acids. Optionally, the sample may enter a downstream neutralization chamber where the pH of the sample is adjusted to the appropriate level as described herein. The lysed or "extracted" sample containing target nucleic acids then is split into three samples, each of which enters one of three separate downstream channels 425a, 425b, or 425c. Downstream channels 425a, 425b, and 425c each lead to separate nucleic acid amplification and detection wells, 470a, 470b, and 470c for performing separate molecular assays. Outlet well 499 provides the user with access to the amplified products.

FIGS. 5A-B depict cross-sectional views of alternative embodiments of optional composite membrane 140. As shown in FIG. 5A, the composite membrane may be comprised of two membranes, membranes 142 and 144. Membranes 142 and 144 may comprise the same or different materials. In one embodiment, the membrane 142 comprises a material that activates blood coagulation, such as glass fibers. In one embodiment, the second membrane 144 may be selected to provide particle-separation functions. In this embodiment, membrane 144 may comprise a filter with a pore size of around 1-2 μm in order to selectively remove red blood cells and white blood cells from the liquid sample. Such membranes may include, but are not limited to, asymmetric and non-asymmetric membranes comprised of polysulfone (manufactured by PALL, Inc.). The two or more membranes may be stacked one on top of the other in device 110. In operation, a blood sample is placed in sample inlet 130. When a drop of whole blood is applied to the device 110, the blood sample is drawn into membrane 142, which causes the blood to clot. Under negative pressure, the clotted sample is further drawn into second membrane 144, which retains the clotted and particulate matter while the liquid serum sample passes through the membrane into voids 182 and 184. The volume of voids 182 and 184 is sufficiently small such that the separated serum sample moves by capillary flow into the first end 122 of the microfluidic channel.

An alternative embodiment of the composite filter is shown in FIG. 5B. As depicted, composite filter 146 comprises a single membrane comprising a plurality of different fiber types, at least one of which promotes the coagulation of unclotted blood. Fibers selected for the composite filter medium include, but are not limited to, cotton linter fibers, glass microfibers, polyester (PET) staple fibers, and lower melting polyester binder fibers. Polyester staple fibers of about 1.5 denier (wherein "denier" is a term of art that refers to a unit that describes the thickness and length of a fiber) and about 0.25-in length may be the backbone of the filter to provide the gross structure of the membrane. Optionally, cotton linter fibers may be used to provide a readily wettable capillary network to passively draw the blood through the filter. Glass microfibers of about 0.40 μm mean fiber diameter may produce the fine pore structure needed for cell and particle separation. Fibers may be joined by woven or nonwoven means. Nonwoven filters may be constructed by wetlaid, spunbonded, or meltblown means. To increase strength, polyester binder fibers may optionally be added to the composite membrane.

As an alternative embodiment of the present invention, the composite membranes of FIGS. 5A-B may further contain one or more activators of blood coagulation. Blood coagulation activators known in the art include, but are not limited to, thrombin, snake venoms, such as Russells viper venom, platelet activating factor (PAF or β-Acetyl-y-O-alkyl-L-∂-phosphatidylcholine), collagen, materials bearing multiple negative charges on their surfaces, such as borosilicate flakes or hallow beads, and aluminum-silicate mineral clays, such as kaolin.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Patent Application Nos. 61/820,573; 61/820,582 and 61/820,587; each of which was filed May 7, 2013, are incorporated herein by reference, in their entireties. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A microfluidic device comprising:
a microfluidic channel having a first end and a second end;
a sample inlet fluidly connected to the first end of the microfluidic channel and configured for receiving a test sample;
a clay treatment chamber fluidly connected to said microfluidic channel, wherein said clay treatment chamber contains a clay mineral reagent;
a sample lysis chamber fluidly connected to said clay treatment chamber, wherein said sample lysis chamber contains an alkaline solution;
one or more sample nucleic acid amplification or detection wells, or combinations thereof, fluidly connected to said sample lysis chamber; and
and one or more sample outlets,
wherein said clay treatment chamber is upstream of said sample lysis chamber and said one or more sample nucleic acid amplification or detection wells, and wherein said device is configured such that said test sample exits said clay treatment chamber and enters said sample lysis chamber, thereby contacting said test sample with said alkaline solution to release target nucleic acids.

2. The microfluidic device of claim 1, wherein the clay mineral comprises a kaolinite, smectite, or illite clay mineral.

3. The microfluidic device of claim 1, wherein the clay mineral comprises talc.

4. The microfluidic device of claim 1, wherein the clay mineral comprises halloysite.

5. The microfluidic device of claim 1, wherein the clay mineral comprises bentonite.

6. The microfluidic device of claim 1, wherein the clay mineral comprises a synthetic clay mineral.

7. The microfluidic device of claim 6, wherein the synthetic clay mineral is laponite.

8. The microfluidic device of claim 1, wherein the alkaline solution comprises KOH, NaOH, or LiOH.

9. The microfluidic device of claim 8, wherein the alkaline solution comprises KOH.

10. The microfluidic device of claim 1, further comprising a neutralization chamber downstream of the lysis chamber, wherein the neutralization chamber contains an acidic reagent.

11. The microfluidic device of claim 10, wherein the acidic solution comprises $HCl$, $C_2H_4O_2$, or $H_2SO_4$.

12. The microfluidic device of claim 1, wherein the test sample comprises one or more infectious agents.

13. The microfluidic device of claim 12, wherein the one or more infectious agents are viral agents.

14. The microfluidic device of claim 1, wherein the test sample comprises at least two viral agents.

15. The microfluidic device of claim 1, wherein the test sample comprises a DNA virus and an RNA virus.

16. The microfluidic device of claim 15, wherein the DNA virus is HBV.

17. The microfluidic device of claim 15, wherein the RNA virus is HCV or HIV.

18. The microfluidic device of claim 1, wherein the test sample is selected from the group consisting of blood, plasma, serum, urine, saliva, sputum, respiratory lavage, tears, and tissue swabs.

19. The microfluidic device of claim 1, wherein the test sample is selected from the group consisting of blood, plasma, and serum.

20. The microfluidic device of claim 1, further comprising an on-device pump fluidly connected to the second end of the microfluidic channel.

21. The microfluidic device of claim 1, further a comprising a composite membrane interposed between the sample inlet and the first end of the microfluidic channel, wherein the composite membrane is capable of removing selected particles from blood.

22. The microfluidic device of claim 21, wherein the composite membrane comprises a material that activates blood coagulation.

23. The microfluidic device of claim 22, wherein the composite membrane comprises a glass filter.

* * * * *